US011443164B2

(12) United States Patent
Dalli et al.

(10) Patent No.: US 11,443,164 B2
(45) Date of Patent: Sep. 13, 2022

(54) EXPLANATION AND INTERPRETATION GENERATION SYSTEM

(71) Applicant: UMNAI Limited, Ta' Xbiex (MT)

(72) Inventors: Angelo Dalli, Floriana (MT); Olga Maximovna Finkel, St Julians (MT); Matthew Grech, San Gwann (MT); Mauro Pirrone, Kalkara (MT)

(73) Assignee: UMNAI Limited, Ta' Xbiex (MT)

( * ) Notice: Subject to any disclaimer, the term of this patent is extended or adjusted under 35 U.S.C. 154(b) by 0 days.

(21) Appl. No.: 17/500,146

(22) Filed: Oct. 13, 2021

(65) Prior Publication Data

US 2022/0114417 A1    Apr. 14, 2022

Related U.S. Application Data

(60) Provisional application No. 63/091,456, filed on Oct. 14, 2020.

(51) Int. Cl.
| | |
|---|---|
| *G06N 3/04* | (2006.01) |
| *G06F 16/28* | (2019.01) |
| *G06F 17/18* | (2006.01) |
| *G06N 3/08* | (2006.01) |

(52) U.S. Cl.
CPC ......... *G06N 3/0427* (2013.01); *G06F 16/284* (2019.01); *G06F 17/18* (2013.01); *G06N 3/08* (2013.01)

(58) Field of Classification Search
None
See application file for complete search history.

(56) References Cited

PUBLICATIONS

Arechiga, Nikos, et al. "Better AI through logical scaffolding." arXiv preprint arXiv: 1909.06965 (2019). (Year: 2019).*

* cited by examiner

*Primary Examiner* — David R Vincent
(74) *Attorney, Agent, or Firm* — Maier & Maier, PLLC

(57) ABSTRACT

An exemplary embodiment provides an explanation and interpretation generation system for creating explanations in different human and machine-readable formats from an explainable and/or interpretable machine learning model. An extensible explanation architecture may allow for seamless third-party integration. Explanation scaffolding may be implemented for generating domain specific explanations, while interpretation scaffolding may facilitate the generation of domain and scenario specific interpretations. An exemplary explanation filter interpretation model may provide an explanation and interpretation generation system optional filtering and interpretation filtering and briefing capabilities. An embodiment may cluster explanations into concepts to incorporate information such as taxonomies, ontologies, causal models, statistical hypotheses, data quality controls, domain specific knowledge and allow for collaborative human knowledge injection. An embodiment may include a flexible presentation layer, user model and a goal-plan-action system to enable practical and useful actionable explanations to be generated.

30 Claims, 13 Drawing Sheets

Expressive Boundary of Interpretable Models, Neural Networks and INNs

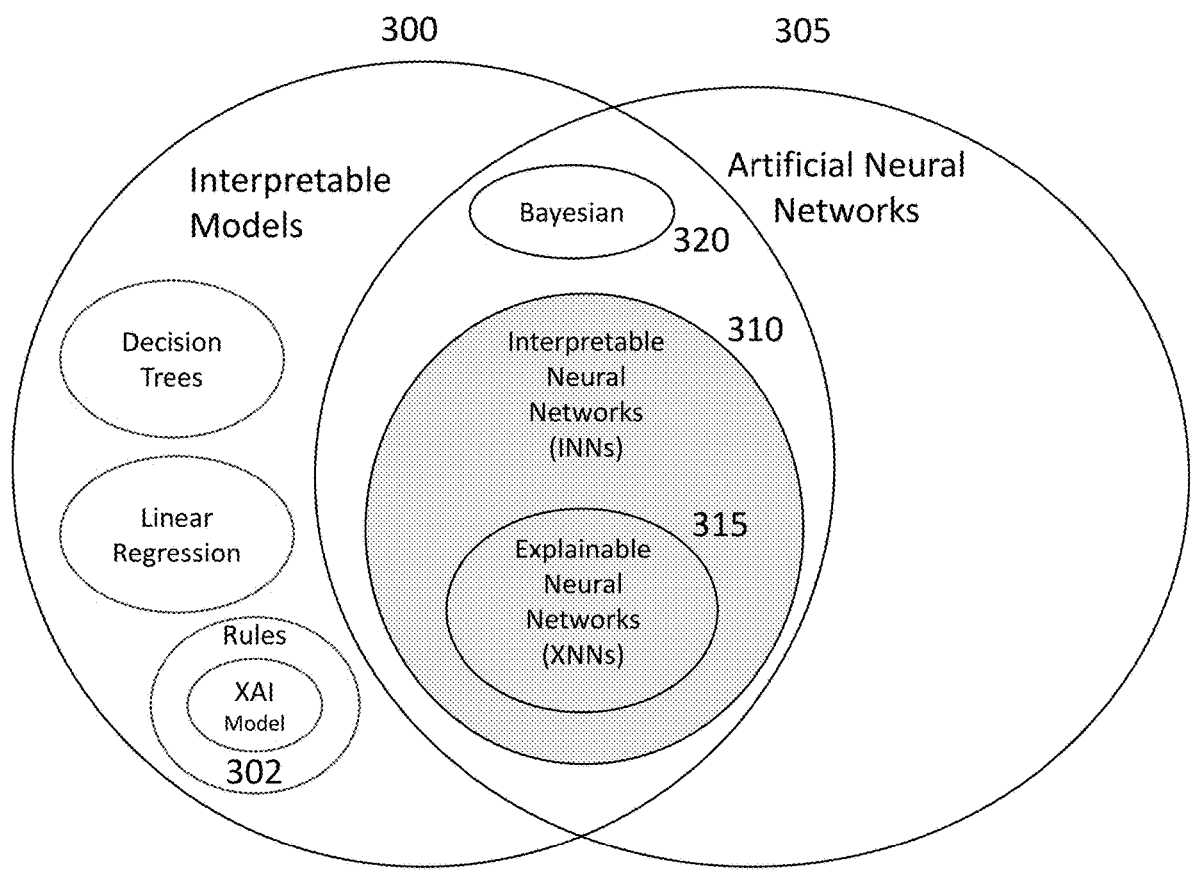
Figure 1 – Expressive Boundary of Interpretable Models, Neural Networks and INNs

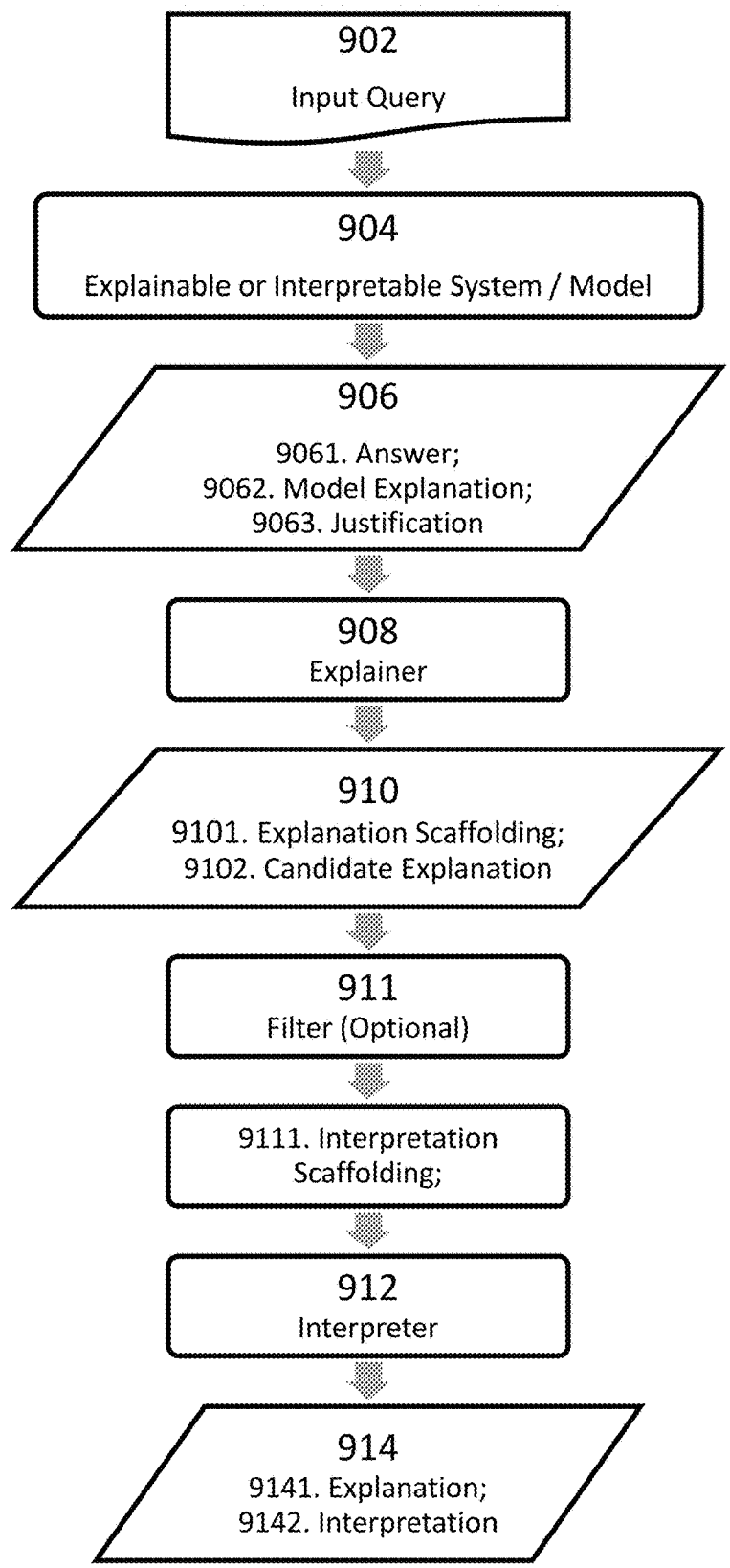
Figure 2 – Exemplary Explanation and Interpretation Process and Outputs

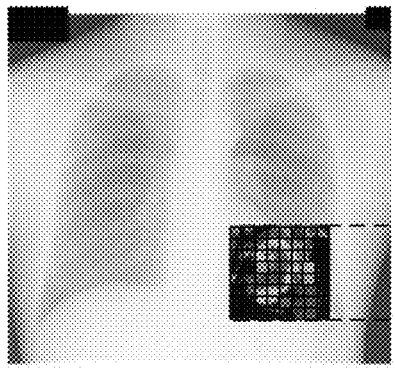
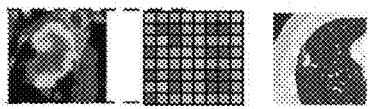
Figure 3 – Example of EIGS output from an XNN, CNN-XNN model fusion

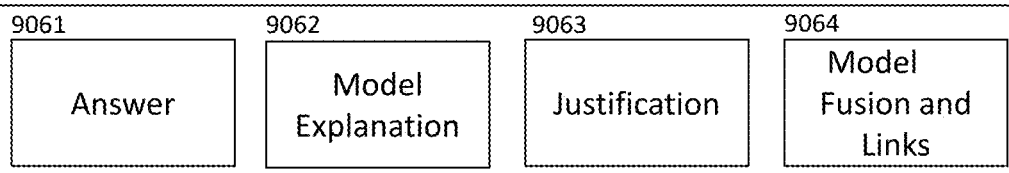
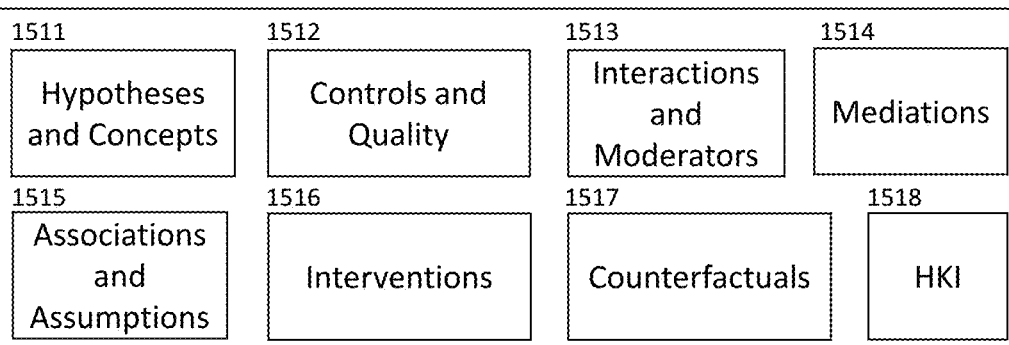
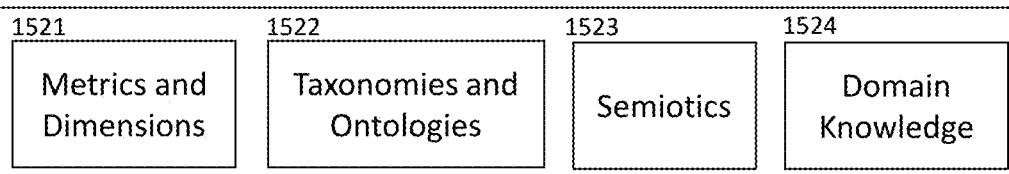
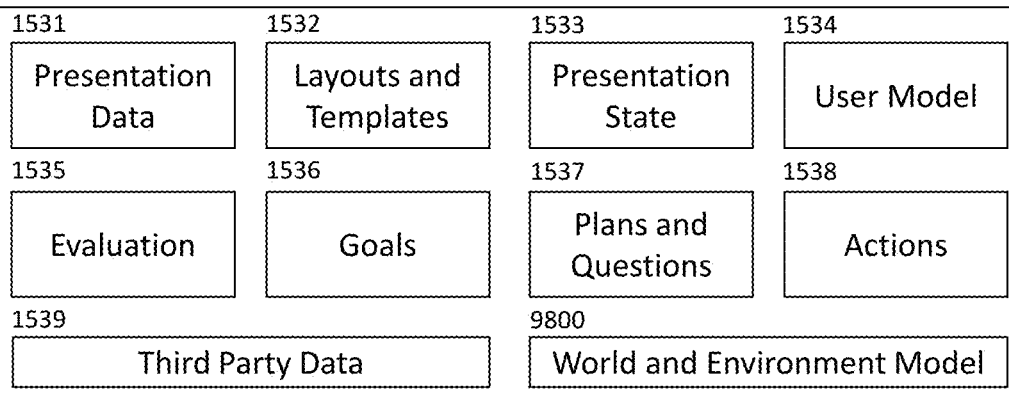
Figure 8 – Explanation Scaffolding Structure 9111 Interpretation Scaffolding

9112 Explanation and Interpretation Scenario Component

9101 Explanation Scaffolding

9113 Interpretation Scenario

1540 Framing, Protocol and Contextual Component

| 1541 Interpretation Framing | 1542 Interpretation Rules and Procedures | 1543 Interpreter Beliefs | 1544 Interactive Context |
|---|---|---|---|
| 1545 Interpretation Templates | 1546 Interpreter Domain Knowledge | 1547 Interpretation Brief | 1548 Protocol Context |

1550 Interpretation Model Component

| 1551 Scenario Model | 1552 Interpretation Model | 1553 Selection Model | 1554 Conflict Resolver |
|---|---|---|---|

Figure 9 – Interpretation Scaffolding Structure

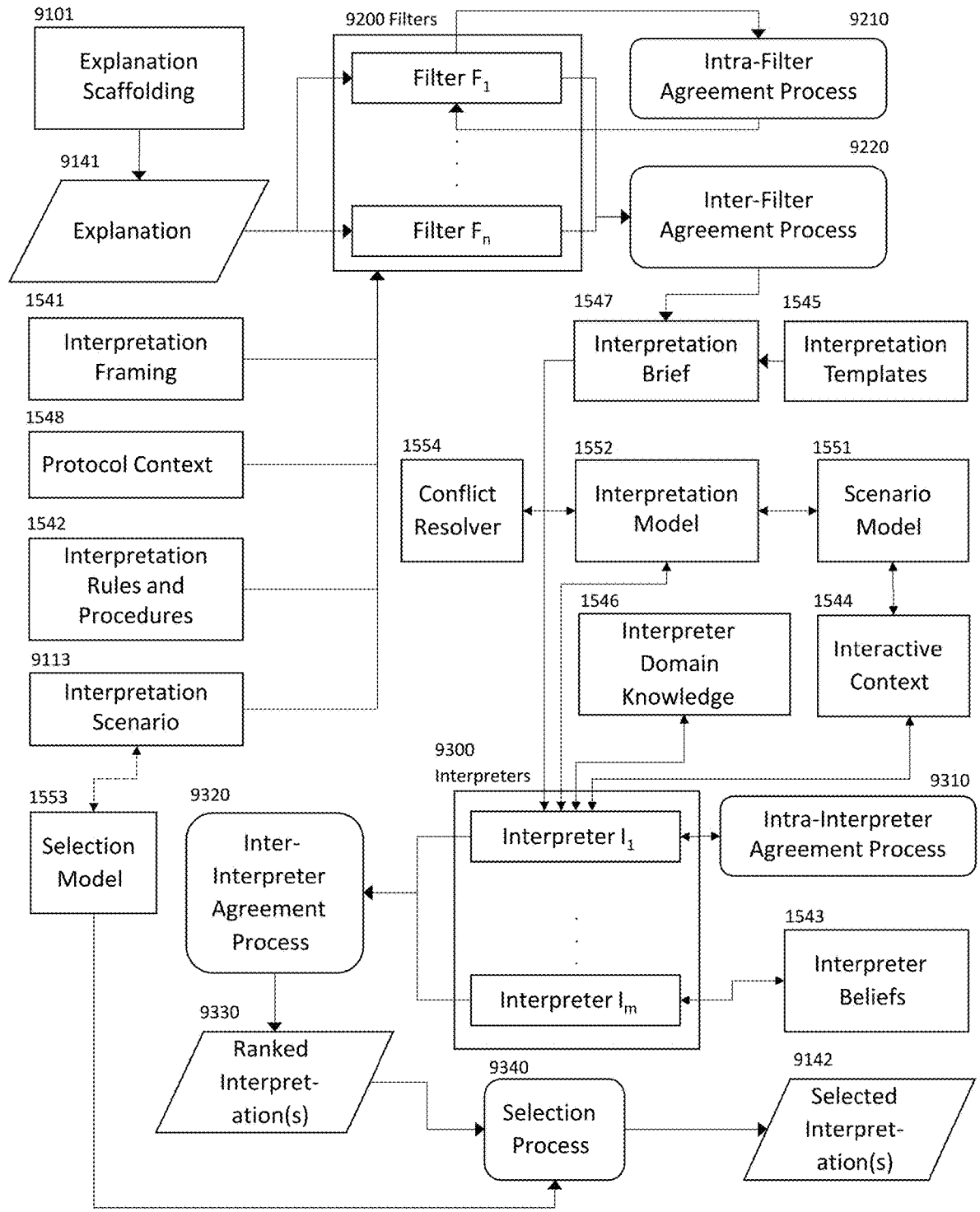
Figure 10 – Explanation Filter Interpretation (EFI) Model

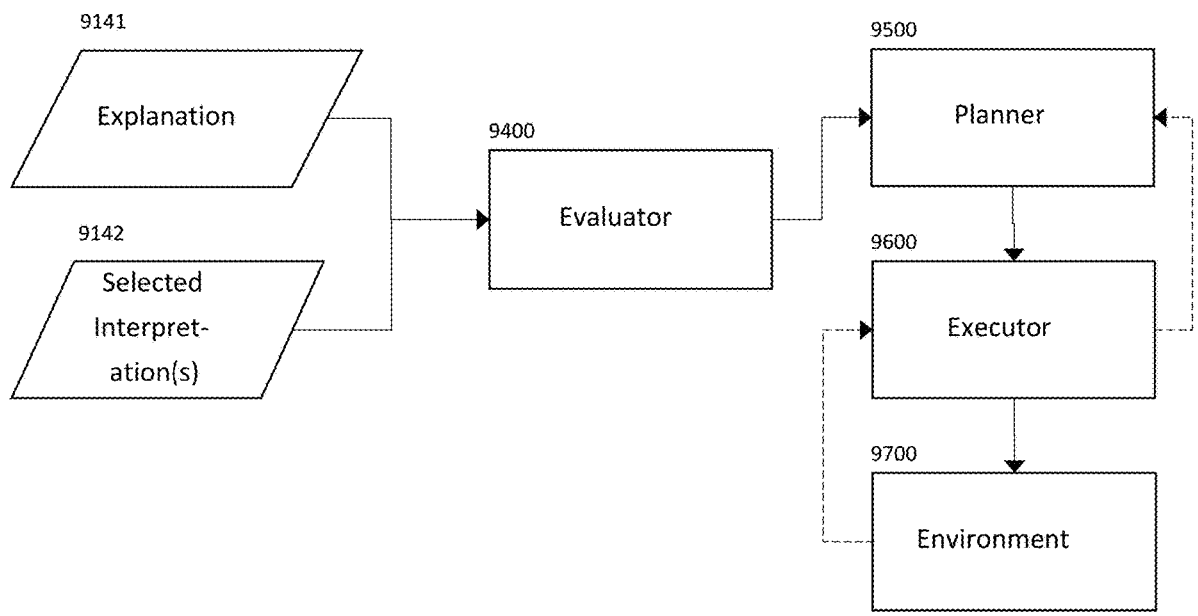
Figure 11 – Application of Explanation or Interpretation in an Actor Model Type of System

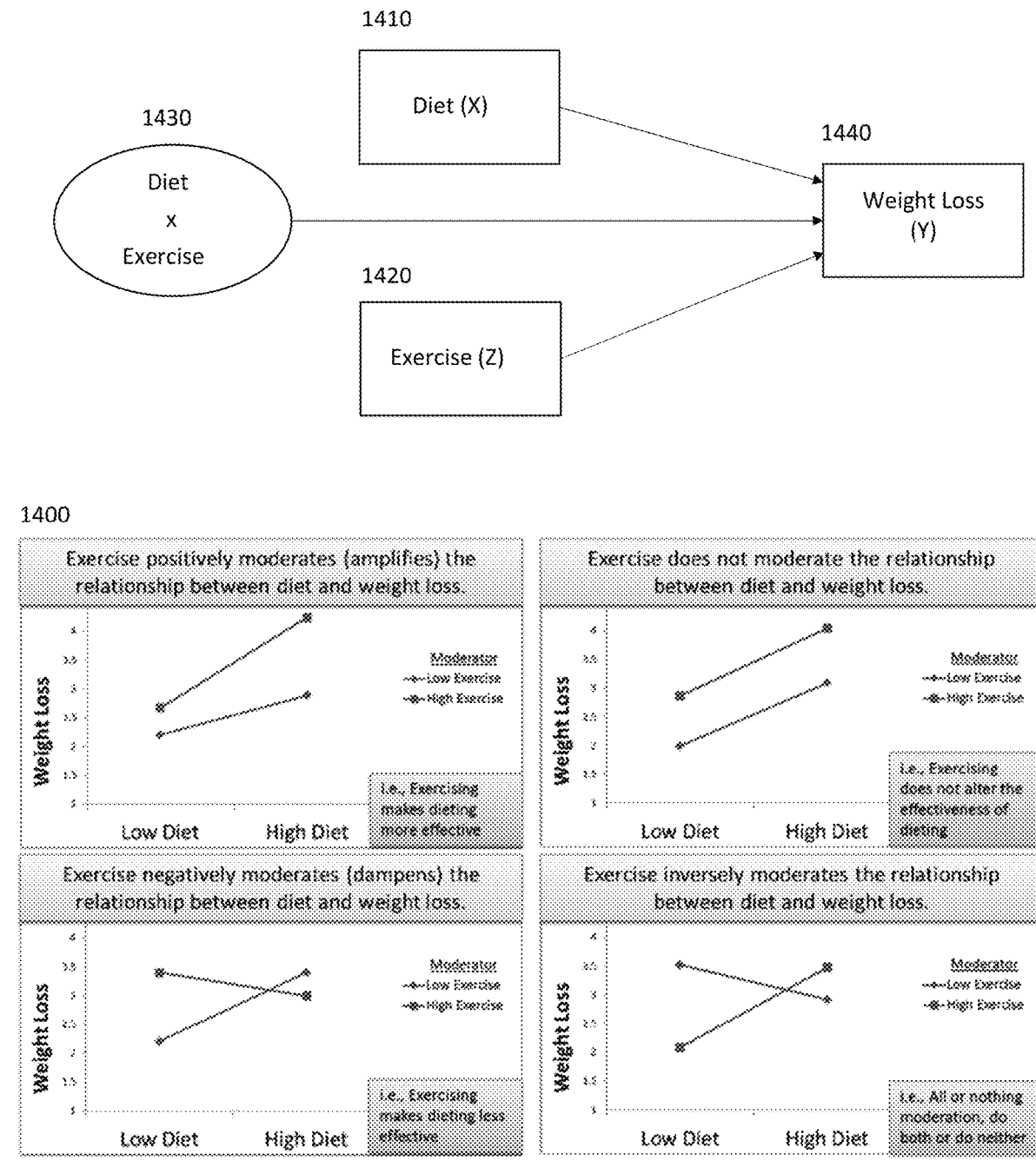
Figure 12 – Interaction Visualization of Causal Effects for an Example Causal DAG diagram. Adapted from (Gaskin, 2016)

EXPLANATION AND INTERPRETATION GENERATION SYSTEM

CROSS-REFERENCE TO RELATED APPLICATIONS

The present patent application claims benefit and priority to U.S. Provisional Patent Application No. 63/091,456 entitled "EXPLANATION AND INTERPRETATION GENERATION SYSTEM" filed on Oct. 14, 2020, which is hereby incorporated by reference into the present disclosure.

FIELD

An exemplary embodiment relates to the field of artificial intelligence and machine learning.

BACKGROUND

Recent advancements in machine learning techniques, specifically deep learning, combined with the highly scalable cloud resources has resulted in artificial intelligence algorithms outperforming humans (Berner et al., 2019), and achieving high accuracies in different areas such as cancer detection (Araujo et al., 2017; Chon et al., 2017) and real-time object detection (Ren et al., 2015).

Despite the recent achievements of deep learning techniques, these systems are not perfect and are known to make mistakes. The result of these mistakes is often unexplainable in most of the cases as the complexity of a deep neural network (DNN) makes it difficult for a researcher to explain the cause of a misclassification. Deep neural network architectures, such as convolutional neural networks (CNN) (Krizhevsky et al., 2012), operate as a black-box, and as a result do not provide valuable information on the decisions that were taken in order to reach a specific result.

The DARPA XAI Program (Gunning, 2016) has analyzed a wide variety of machine learning systems, including rule-based expert systems, case-based reasoning systems, black-box machine learning systems, Bayesian classifiers, quantitative models, statistical models, and decision trees.

There is also a considerable variety of applications, such as gesture classification, image classification, text classification, decision-making, program debugging, music recommending, financial accounting, strategy gaming, command training, robotic agents, non-player character agents, and patient diagnosis.

The DARPA XAI program also published two high quality background survey papers about the state of the art in XAI solutions and XAI in general (Mueller et al, 2019). These two publications and the background material referenced in them present an accurate and comprehensive snapshot of the state-of-the-art in the field as of the time of writing. In particular, Mueller presents a summary of key papers that are especially pertinent to XAI.

The DARPA XAI program published a comprehensive survey of existing XAI explanation evaluation metrics (Hoffman et al., 2018), which together with an evaluation survey (Mohseni, Zarei and Ragan, 2020) presents an accurate and comprehensive snapshot of the state-of-the-art in the field.

(Hong et al., 2020) concluded that machine learning practitioners define interpretability as the alignment of the system machine learning model with the human mental model, where the mental models may vary between multiple stakeholders who are exposed to the model. (Hong et al., 2020) also concludes that machine learning practitioners see black-box models as hard to interpret or having overly complex logic that make it difficult or impossible to guarantee a high level of trust.

(Hong et al., 2020) further illustrates how the machine learning practitioners highlight the lack of interpretable tools for understanding how a model makes a prediction, understanding the root cause of a particular prediction, identification of interpretable decision boundaries, and identifying the general structure of a model as barriers to XAI models.

SUMMARY

According to at least one exemplary embodiment, a method and system and apparatus for generating explanations and interpretations from machine learning systems may be shown and described. An exemplary embodiment may present the generated explanations and interpretations using various presentation formats and layouts including but not limited to human readable natural language text, graphical or visual formats, audio, speech, haptic, video, time series, stereoscopic images, LIDAR, RADAR, SONAR, multi-spectral data, 3D data and any other application that needs to predict, anticipate and explain its past, present, and future state. The generated explanations and interpretations may be presented in different styles, and may be conclusive, detailed, or a summary.

An exemplary embodiment may present explanations and interpretations aimed at different levels of user expertise. Users may receive explanations personalized according to industry specific needs and may understand when the exemplary system is wrong as well as a reasoning behind the system's conclusion. Statistical, causal and symbolic knowledge may be used for generating the explanations and interpretations. Taxonomies, ontologies, external knowledge, and domain-specific knowledge may be used for generating the explanations and interpretations. Taxonomies and ontologies may be used to fuse multiple XAI models. An exemplary embodiment may also implement causal logic. Learnt concepts may be extracted from human generated explanations. An extensible explanation architecture may allow for third-party integration. It is further contemplated that an exemplary embodiment may employ the concept of anchor terms and anchor concepts, such as used in Comparative Causal Mapping (CCM), to indicate what explanatory elements are most important to a particular user or user group.

An exemplary embodiment may generate domain-specific explanations and domain and scenario specific interpretations. An exemplary explanation filter interpretation (EFI) model may provide an explanation and interpretation system. An exemplary EFI may include filtering and interpretation filtering and briefing capabilities.

In an exemplary embodiment, different types of explanations and meta-explanations may be clustered into concepts and concept hierarchies. Human knowledge injection may be implemented. Further, an exemplary embodiment may provide a novel domain-specific optimization method for explainable machine learning systems that improves the quality of explanations and interpretations in a semi-supervised or unsupervised manner. Another exemplary embodiment may provide a novel data format agnostic kernel labelling method that may associate human readable labels with data formats such as images or 3D scans that are not textual in nature.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which:

FIG. 1 is an exemplary embodiment of an expressive boundary of a model;

FIG. 2 is an exemplary embodiment of an exemplary explanation and interpretation process and outputs;

FIG. 3 is an exemplary embodiment of an EIGS output from an XNN, CNN-XNN model fusion;

FIG. 8 is an exemplary embodiment of an explanation scaffolding structure;

FIG. 9 is an exemplary embodiment of an interpretation scaffolding structure;

FIG. 10 is an exemplary embodiment of an explanation filter interpretation (EFI) model;

FIG. 11 is an exemplary embodiment of an application of explanation or interpretation in an actor model type of system;

FIG. 12 is an exemplary embodiment of an interaction visualization of causal effects for an exemplary causal DAG diagram.

DETAILED DESCRIPTION

Figure 4:
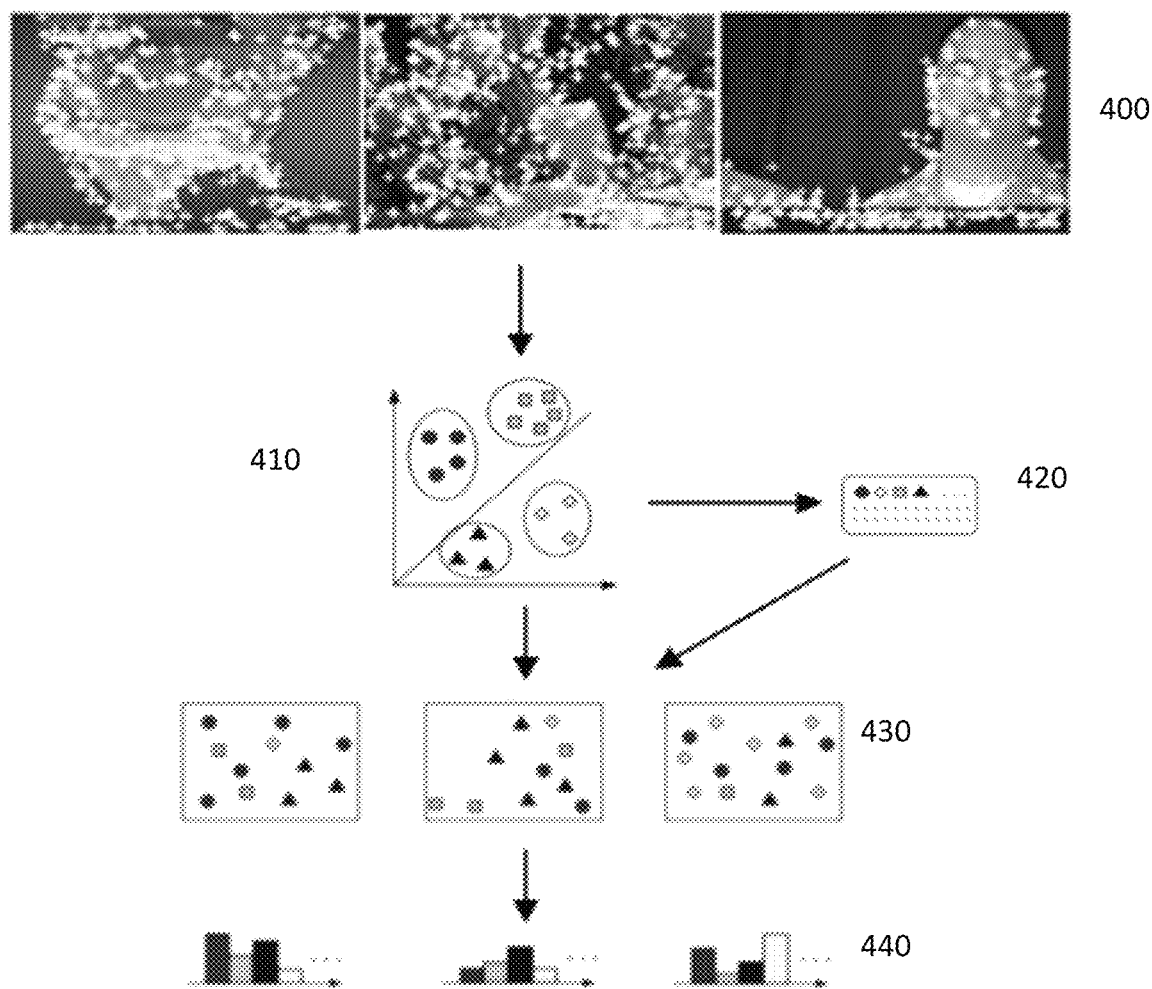
FIG. 4 is an exemplary prior-art embodiment of a bag of visual words.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein are described in terms of sequences of actions to be performed by, for example, elements of a computing device. It should be recognized by those skilled in the art that the various sequences of actions described herein can be performed by specific circuits (e.g. application specific integrated circuits (ASICs)) and/or by program instructions executed by at least one processor. Moreover, several of the exemplary embodiments below may be implemented in software form on conventional computers or embodied by specialized hardware such as reprogrammable FPGA, ASIC, analog/digital electronics, optical-electronic hardware, quantum computers or neuromorphic hardware. Additionally, the sequence of actions described herein can be embodied entirely within any form of computer-readable storage medium such that execution of the sequence of actions enables the at least one processor to perform the functionality described herein. Furthermore, the sequence of actions described herein can be embodied in a combination of hardware and software. Thus, the various aspects of the present invention may be embodied in a number of different forms, all of which have been contemplated to be within the scope of the claimed subject matter. In addition, for each of the embodiments described herein, the corresponding form of any such embodiment may be described herein as, for example, "a computer configured to" perform the described action.

Interpretability is a characteristic that may be defined by an interpreter. The interpreter may be an agent that interprets the system output or artifacts using a combination of (i) its own knowledge and "beliefs", (ii) goal-action plans, (iii) context(s), and (iv) the world environment. An exemplary interpreter may be a knowledgeable human.

An alternative to a knowledgeable human interpreter may be a suitable automated system, such as an expert system, which may be able to interpret outputs or artifacts for a range of applications. For example, a medical expert system, or some logical equivalent such as an end-to-end machine learning system, may be able to output a valid interpretation of medical results in a specific set of medical application domains.

It may be contemplated that non-human interpreters may be created in the future that can partially or fully replace the role of a human interpreter, and/or expand the interpretation capabilities to a wider range of application domains.

There may be two different distinct types of interpretability: (i) Model interpretability, which measures how comprehensible and understandable any form of automated or mechanistic model is, together with its sub-components, structure and behavior; and (ii) output interpretability, which measures how comprehensible and understandable the output of the model is.

Interpretability is thus not a simple binary characteristic, but can be evaluated on a sliding scale ranging from fully interpretable to un-interpretable. Model interpretability may relate to the interpretability of the underlying embodiment, implementation, and/or process producing the output, while output interpretability may relate to the interpretability of the output itself or whatever artefact is being examined.

A machine learning system or suitable alternative embodiment may include a number of model components. Model components may be model interpretable if their internal behavior and functioning can be fully understood and correctly predicted, for a subset of possible inputs, by the interpreter. In an exemplary embodiment, the behavior and functioning of a model component can be implemented and represented in various ways, such as a state-transition chart, a process flowchart or process description, a behavioral model, or some other suitable method.

Model components may be output interpretable if their output can be understood and correctly interpreted, for a subset of possible inputs, by the interpreter.

An exemplary embodiment may deemed to be (i) globally interpretable if it is fully model interpretable (i.e. all of its components are model interpretable), or (ii) modular interpretable if it is partially model interpretable (i.e. only some of its components are model interpretable). Furthermore, an entire exemplary machine learning system or suitable alternative embodiment may be locally interpretable if all of its output is output interpretable.

An exemplary embodiment may provide a grey-box, which may be a hybrid mix of a black-box with white-box characteristics. A grey box may have characteristics of a white-box when it comes to the output, but that of a black-box when it comes to its internal behavior or functioning.

A white-box may be a fully model interpretable and output interpretable system, which can achieve both local and global explainability, making them the most explainable and fully interpretable in terms of both their internal function and their output. An XNN is an example of an output interpretable and a fully model interpretable system.

A black-box may be output interpretable but not model interpretable, and may in some cases achieve limited local explainability, making them the least explainable with little to no explainability capabilities and minimal understanding in terms of their internal function. A deep learning neural network may be an output interpretable yet model uninterpretable system.

A grey-box is a partially model interpretable and output interpretable system, and may be partially explainable in terms of internal function, and interpretable in terms of output. A grey-box may be between a white-box and a black-box on a scale of most explainable and interpretable (white-box) to least explainable and interpretable (black-box). Grey-box systems can also have a level of modular interpretability, since some of their components may be model interpretable. An interpretable neural network (INN) is an example of an output interpretable and partially model interpretable system.

An exemplary embodiment may be model interpretable. The interpretable behavior may be used for controlling the final output result. For instance, in a simple linear regression model, the coefficients may be used for the resulting prediction output. In decision trees, the nodes may determine the decision boundaries, which may directly control the final result output through the leaf nodes. An interpretable system or model may be capable of generating a model explanation accompanying the answer output, in a suitable format such as a generalized rule-based format or any logical equivalent.

In an exemplary INN, the relevance estimators combined with the feature transformations may compute the result output and simultaneously generate an explanation in a local manner.

Interpretable models may be global or local. For instance, linear regression and decision trees may be globally explainable. INNs may achieve local explainability within one partition, however through the use of multiple partitions, global explainability may also be achieved. Additionally, INNs may be combined with black-box logic within the network itself. In that case, INNs may function as a locally explainable model, since global explainability may require all the components of the model to be fully-white-box.

For an exemplary globally interpretable system, each individual component may be understandable individually without having to undertake an analysis of the entire system as an indivisible whole. For example, an exemplary XNN may be a globally explainable system, and thus may allow for conversion into several different formats while still retaining logical equivalence. A conversion may not be possible with models that are only capable of providing local interpretability.

FIG. 1 illustrates the expressive boundaries of interpretable models and artificial neural networks in general with various examples of machine learning implementations. The expressive boundary of interpretable models is outlined by set 300. Traditional interpretable models include decision trees, linear regression, quantile regression, inference networks, belief networks and rules. An induced XAI Model 302 may also be an interpretable model. The expressive boundaries of Artificial Neural Networks (ANNs) are outlined by set 305. Within the set 305, there are various exemplary connectionist model implementations including deep learning networks, Bayesian networks and so on. Some of the systems within set 305 may be black-box and others may be interpretable, or logically equivalent to INNs. Alternatively, it may be possible to have an interpretable model, which is a connectionist model, a neural network or some equivalent, but not an INN, as shown in set 320, for example, a Bayesian Network. Finally, INNs may act either as a fully white-box model, when being a logically equivalent network to fully explainable models such as XNNs, as shown in set 315, or may act as a gray-box model by providing local explainability as shown in set 310. Predictive INNs can be partially gray-box models with part of the model being implemented as a black-box. XTTs and predictive XNNs can be white-box models in the vast majority of cases but can also be implemented partially as a gray-box. XNNs may be a fully contained subset of INNs, while INNs themselves may be a fully contained subset of ANNs. XNNs may fall within set 315 if implemented as a fully white-box model, or in set 310 if implemented as a grey-box model. XSNs fall within set 302, as they are not an ANN yet still fully interpretable and explainable.

An exemplary embodiment may provide an explanation and interpretation generation system (EIGS). An EIGS may be based on an exemplary explanation and interpretation generation pipeline illustrated in FIG. 2. The exemplary embodiment in FIG. 2 may be distinguished by the three part process of explanation, filtering and interpretation, where the filtering step may be optional. An embodiment that produces at least an answer 9061 and its explanation 9141 from an input query 902 may be logically equivalent to the exemplary pipeline in FIG. 2 to some extent.

An exemplary EIGS may be applicable to explainable or interpretable systems and models. Examples of explainable or interpretable systems include, but are not limited to, those based on induced eXplainable artificial intelligence (XAI) models, Interpretable Neural Nets (INNs), eXplainable Neural Nets (XNN), eXplainable Transducer Transformers (XTT), eXplainable Spiking Nets (XSN), eXplainable Memory Net (XMN), eXplainable Reinforcement Learning (XRL), eXplainable Generative Adversarial Network (XGAN), eXplainable AutoEncoders (XAED), eXplainable CNNs (CNN-XNN), Predictive eXplainable XNNs (PR-XNNs), Interpretable Neural Networks (INNs) and related grey-box models which may be a hybrid mix between a black-box and white-box model. Although some examples may reference one or more of these specifically (for example, only XRL or XNN), it may be contemplated that any of the embodiments described herein may be applied to XAIs, XNNs, XTTs, XSNs, INNs, XMNs, and the like interchangeably. An exemplary embodiment may apply fully to the white-box part of the grey-box model and may apply to at least some portion of the black-box part of the grey-box model. It may be contemplated that any of the embodiments described herein may also be applied to INNs interchangeably.

An exemplary EIGS may be different than a general purpose explanation and interpretation production and invention system of the type that may result from an Artificial General Intelligence (AGI) system.

An exemplary embodiment may begin with an input query 902, representing a data sample, scenario or other question which is currently being examined, which may be then processed through three components: the explainable or interpretable system/model 904, the explanation module or explainer 908, and the interpretation module or interpreter 912. Each of the three components may produce different outputs which are input to the next component in the process pipeline. It may be contemplated that the input query 902 is not limited to a specific data sample or scenario, and may relate to the entire model (global model explainability) or a modular explanation which deals with a specific component of the interpretable model.

The explainable or interpretable system/model 904 may produce a model explanation output 906 including a combination of an answer 9061, together with an optional model explanation 9062 of that answer, and optionally a justification 9063 of the answer and/or its model explanation. The justification 9063 of the answer and/or its model explanation may be an explanation of the model explanation (i.e. a meta-explanation) that gives additional information about the assumptions, processes and decisions taken by the explainable or interpretable system/model 904 when outputting such answer and/or model explanation.

The explainer or explanation module 908 may produce an explanation scaffolding 9101, together with an optional candidate explanation 9102. In an exemplary embodiment, the candidate explanation may be generated as a result of processing of the explanation scaffolding 9101 and can be used to evaluate the contents of the explanation scaffolding in some form of iterative process involving unsupervised or supervised learning and optimization. The explanation scaffolding 9101 and the candidate explanation 9102 may be packaged together as the explanation 910, which is effectively the explainer 908 output.

The filter 911 is an optional component that may transform and filter the explanation scaffolding 9101 and the interpretation scaffolding 9111, for example, after the explainer 908 has produced output but before the interpreter 912 starts.

The interpreter 912 may produce an explanation 9141, together with an optional interpretation 9142 of that explanation, using an interpretation scaffolding 9111.

The end result 914 of the explanation process may include either an explanation and/or its interpretation, which may be consumed by a human user, another application, another system component forming part of a larger embodiment, or some other automated system.

Note that FIG. 2 is just an exemplary pipeline and may be implemented in various alternative embodiments that may omit or combine one or more components, and/or execute them in a different order and sequence. For example, in a practical implementation embodiment, it may be contemplated that both components 908 and 912 can be omitted together with their respective outputs 908 and 914. In another exemplary embodiment, components 908 and 912 can be combined together as a single component that produces a combination of the outputs 908 and 914. In another contemplated embodiment, a simplified implementation of the interpreter 914 may take the candidate explanation 9102 and outputs it as the explanation 9141.

It may be contemplated that in the case of a global (i.e. model level) explanation or a query-less application embodiment, even the input query 902 can be omitted without losing the logical equivalence to the exemplary pipeline in FIG. 2 to some extent.

It may be contemplated that some combination of outputs in FIG. 2 may be combined together or omitted altogether in a practical embodiment. For example, the justification 9063 may be deemed optional in some applications, while the interpretation 9142 may be left for a human interpreter or expert to create instead of an automated system.

An interpretable machine learning system may be thoroughly understood and have its functionality and internal behavior (model interpretability), answers (output interpretability) and explanations interpreted and understood by an interpreter. The final explanations accompanying the answers might not require further post-hoc processing on their core structure, although additional cycles of processing to add syntactic and semantic information and to contextualize and personalize the explanation may be contemplated, as illustrated in FIG. 2, where the explanation 9141 goes through different stages of transformation and enhancement before it gets to a final stage.

The explanation scaffolding 9101 can also store audit data in appropriate components such as the actions 1538 or the evaluation 1535 components, or via an independent audit system plugged in to the third-party data 1539 extension component.

The interpretation scaffolding 9111 can also store audit data in appropriate components such as the interactive context 1544 or the protocol context 1548 components.

The audit and explanation advantages of an exemplary EIGS-based system may be superior to existing solutions, which are either implemented in a hard-coded and inflexible manner to comply with regulations, or may be flexible while relying on a black-box, rendering them impossible to use in a regulated application.

An exemplary embodiment may allow for a practical solution that incorporates modern, flexible machine learning methods within a white-box explainable and interpretable system that can be used in a regulated application.

The explanation scaffolding may be used to provide a practical embodiment of explanations and explanatory information for explainable machine learning systems and other automated systems.

FIG. 8 illustrates an exemplary structure for an explanation scaffolding 9101. The explanation scaffolding 9101 may be structured into four exemplary components: the model explanation component 906, the hypothetical and causal component 1510, the semiotics, taxonomical, and ontological component 1520, and the scenarios, interaction, and presentation component 1530.

The model explanation component 906 may include the answer 9061, model explanation 9062, justification 9063, and model fusion and links 9064 components.

The answer 9061, together with an optional model explanation 9062 of that answer, and optionally a justification 9063 of the answer and/or its model explanation may be produced by the explainable or interpretable system or model 904. The justification 9063 may be used by system users to understand when the model 904 may be wrong.

The model fusion and links component 9064 may be used to store model fusion and linkage information that can be utilized to fuse answers, model explanations and justifications coming from a number of models 904 including but not limited to models hosted locally, remotely, via a number of data transmission networks, on the edge, and embedded systems, which are further deployed as a single or distributed model, or as ensembles. Models 904 may be implemented in a mixture of software running on general purpose hardware, software running on dedicated hardware, and various hardware implementation options or some other suitable implementation.

The model fusion and links component 9064 may also be used to store additional metadata and information associated with a number of models 904 that may be present in the explanation scaffolding 9101 and/or the interpretation scaffolding 9111. In an exemplary embodiment, component 9064 may be used to link to any of, or a combination of, a data lake, a data cube, a distributed database system, a relational database, a columnar database, a streaming data source, realtime sampled data, a file system, or another adequate data source or combination of data sources.

Model fusion and links component 9064 may also be used in conjunction with the taxonomies and ontologies component 1522 to utilize taxonomical and ontological information to aid in the fusion of multiple models 904 and their accessible datasets.

The hypothetical and causal component 1510 may include the hypotheses and concepts 1511, controls and quality 1512, interactions and moderators 1513, mediations 1514, associations and assumptions 1515, interventions 1516, counterfactuals 1517, and HKI 1518 components.

The hypothetical and causal component 1510 within the explanation scaffolding 9101 provides a practical solution for the integration of structural equation models (SEM), structural causal models (SCM) and causal directed acyclic graph (DAG) diagrams that may be used to model cause-and-effect within grey-box and white-box explainable machine learning systems.

Exemplary causal models that may be partially or wholly used in the implementation of causal component 1510 and/or the entire EIGS, may include a combination of Pearl's structural causal models and associated derivations and variations, dynamic causal models and associated Bayesian model comparison methods and variations, granger causal models, relativistic causal models arising from special and general relativity, and other suitable implementations that allow machine learning to represent cause-and-effect.

The hypotheses and concepts component 1511 may contain information about any applicable hypotheses currently applicable to the explanation and its subsequent interpretation. The hypotheses may also be subsequently evaluated against results from testing performed by the model 904. Hypotheses may optionally be used in order to structure the justification 9063 and the model explanation 9062.

Hypotheses that may be used in the implementation of hypotheses and concepts component 1511 may include a combination of: (i) trial hypotheses that provide a suggested outcome based on evidence, which needs to be tested and confirmed or rejected; (ii) abductive hypotheses that provide a suggested explanation that needs to be achieved or a goal that needs to be achieved; (iii) statistical hypotheses, of a suitable form such as the null hypothesis and alternative hypothesis pair; (iv) causal hypotheses, that provide a suggestion about whether one or more features recognized by the model 904 is an effect of a cause triggered by an interaction of one or more features recognized by the model 904.

Abductive hypotheses may be implemented via the appropriate abductive logic system appropriate for the specific EIGS embodiment, for example, Pierce's abductive logic system, and so on. Causal hypotheses may be implemented via the appropriate causal logic system appropriate for the specific EIGS embodiment, for example, if using Pearl's structural causal models, the implementation in hypotheses and concepts component 1511 may use a causal DAG, and so on. It is further contemplated that abductive logic systems are utilized in diagnostic type of systems where observed effects are matched to plausible and/or potential causes. In an exemplary embodiment, a medical application may utilize such an abductive logic system in conjunction with causal hypotheses to diagnose a medical condition from observed symptoms and use appropriate hypotheses evaluation methods (such as counterfactual analysis) to recommend potential interventions and courses of action.

Hypotheses evaluation methods may also be implemented as part of hypotheses and concepts component 1511, including but not limited to the evaluation of testability, falsifiability, the level of parsimony and compactness, scope, genericity, specificity, coverage and the degree of fit with existing recognized knowledge-systems.

The hypotheses and concepts 1511 component may also contain sets of concepts and a conceptual framework. Each concept forming part of the concepts set is associated with groupings of one or more hypotheses. The hypotheses may connect concepts by specifying the expected relationships between propositions for the relevant concepts, forming a conceptual framework via the hypothesis connection relationships. An exemplary conceptual framework can incorporate any combination of trial, statistical, and causal hypotheses, suitable items in the explanation scaffolding 9101 and also suitable items in the interpretation scaffolding 9111.

It may be contemplated that hypotheses and concepts component 1511 may be used to cluster different types of explanations into concepts, using a cognitive chunk model, such as the one described in (Doshi-Velez et al., 2017) that details the different aspects that may be taken into consideration in the identification of suitable cognitive chunks.

In an exemplary embodiment, the cognitive chunks may be treated as a non-reducible subset of information within the explanation that are related via a relationship or similar association identified by either the model 904, the answer 9061, model explanation 9062, justification 9063, or the hypothetical and causal component 1510 and its sub-components. Further, the cognitive chunks are in a one-to-one or a one-to-many relationship between hypotheses stored in hypotheses and concepts component 1511.

The controls and quality component 1512 may contain information that may enable the EIGS to achieve a combination of: (i.) generation of output within desired quality parameters; (ii.) obeying compliance constraints within specific tolerance parameters; (iii.) storing and retrieving information about the state of qualitative or quantitative information of all variables and data available to the EIGS and its components such as the Explanation Scaffolding 9101 and Interpretation Scaffolding 9111; (iv.) determining whether the data available to the EIGS and its components are internally consistent; (v.) applying a combination of standardization, data cleansing, data transforms, data profiling, data matching, data linking, data conformity checks, data accuracy checks, data precision checks, data bias checks, and data interpolation methods to the data available to the EIGS and its components; (vi.) applying data privacy and access rules and specifications to the data available to the EIGS and its components; (vii.) triggering actions, modify and configure constraints and activate events and triggers in behavioral models (BMs) or similar systems; (viii.) validating, comparing and analyzing data available to the EIGS and its components in relation to a set of well-defined valid values of reference data to discover new or discrepant values; and (ix.) applying data transforms, timestamp checks, data freshness checks, and/or data retention policy compliance of all data available to the EIGS and its components against a defined service level agreement (SLA).

The EIGS may include various methods to reduce the number of data quality checks, according to exemplary embodiments where these are not included or not required. In an exemplary embodiment, the EIGS may use data from the model fusion and links 9064 to check for the source and reliability of the incoming data source, or from the interpretation framing 1541 or from the interpretation brief 1547 to determine what data quality check can be skipped safely.

In an exemplary embodiment, the EIGS may use controls and quality component 1512 together with semiotics 1523, and domain knowledge 1524 components to perform more complex data quality checks involving domain knowledge, to execute well-known processes and functions held in the domain knowledge against a subset of data available to the EIGS and its components, to perform a combination of: (i.) checks against a specific range of values or static interrelationships; (ii.) checks against aggregated process and functions held in the domain knowledge; (iii.) outlier checks and exception case flagging; (iv.) drift checks against nominal conditions that are prespecified or automatically discovered by a machine learning system; (v.) checks against BAU (business as usual) expectations; (vi.) checks using an explainable autoencoder/decoder (XAED) system for drift, shift and abnormality detection. Checks may be made via a combination of: (i.) simple generic aggregation rules; (ii.) complex logic functions on a group of attributes of data input to the well-known processes and functions held in the domain knowledge; (iii.) automatically discovered checks that have been discovered via a suitable machine learning process ran against the well-known processes and functions held in the domain knowledge.

The controls and quality component 1512 may contain control grouping information that can be used by the causal model utilized in the implementation of hypothetical and causal component 1510 and/or the entire EIGS. The grouping information may be utilized to control for a variable according the different measured values of that variable, to ensure that the variable can no longer act as a confounder. The controlled-for variables may be subsequently treated as input features both to the model 904 and the EIGS in order to separate their effects from explanatory variables that are utilized by the model 904 and/or the EIGS.

The counterfactuals component 1517 may contain information to mitigate the influence of confounders identified by intervention component 1516 without opening back-door paths to unknown confounders that may happen as a result of the application of the control grouping information in control and quality component 1512.

The interaction and moderator component 1513 is a component of the EIGS neurosymbolic architecture, and may contain information about the statistical correlations and causal interactions identified in the model 904, the EIGS and its components. Statistical and causal interactions can be stored as a combination of: (i.) transformations and mappings of subsets of data features against one or more subsets of data features; (ii.) predictions from information embedded in some reconstructed state space, and/or latent space, and/or phase space; (iii.) statistical correlations and interactions and similar type of information; (iv.) causal interactions and similar type of information; (v.) co-occurrence statistics indicative of cause-and-effect; (vi.) estimator functions and estimands together with their resulting estimates.

In interactions and moderators component 1513, the estimator functions may be used to determine an estimate from an estimand, which can be any relevant piece of information identified in the model 904, the EIGS and its components. Estimator functions in the EIGS may be, for example, (i.) a point estimator that gives a single-valued result or a single vector-valued result or a result that can be expressed as a single function, or (ii.) an interval estimator that gives a range of possible values or vectors or functions. In an exemplary embodiment, the model fit evaluation implementation in hypotheses and concepts component 1511 may be used to determine whether the estimator functions in mediations component 1514 have a high level of fit possibly under increasingly specific constraints or a lower level of fit possibly under more generic and widely applicable constraints.

It may be contemplated that interactions and moderators component 1513 implements a suitable resampling method, applicable to any relevant piece of information identified in the model 904, the EIGS and its components, such as bootstrapping (including but not limited to case resampling, Bayesian, smooth, parametric, residual resampling, Gaussian Process, Wild, Block, Poisson, bagging, and aggregation), the jack-knife procedure, or exhaustive and non-exhaustive cross-validation to: (i.) estimate sampling distributions; (ii.) estimate precision and accuracy of sample statistics (medians, variances, bias, confidence intervals, prediction error, percentiles, etc.); (iii.) estimate significance via significance tests or permutation tests; (iv.) validate models using random subsets; (v.) construct alternatives to statistical inference which are transmitted to hypotheses and concepts component 1511. Alternatives transmitted to hypotheses and concepts component 1511 may be used as the basis for the additional creation of a black-box machine learning model in cases where it may not be practical to create a standard white-box statistical or causal parametric model. Exemplary black-box machine learning models may in turn be induced to a white-box model and added to the collection of models 904 in an iterative process. In an exemplary embodiment, different methods may be implemented to estimate the uncertainty inherent in observed data points, such as the XNN prediction network layers, Local Ensemble Transform Kalman Filter (LETKF) and other methods.

In interactions and moderators component 1513, statistical and causal interaction information may be used to discover the presence of moderators within any relevant piece of information identified in the model 904, the EIGS and its components. The EIGS may implement moderators as a categorical or a quantitative variable that affects the direction and/or strength of the relation between the Interactions identified in interactions and moderators component 1513. In an exemplary embodiment, a combination of (i.) a suitable correlation analysis method such as the Pearson product-moment correlation coefficient (PPMCC); or (ii.) a suitable variance analysis method such as ANOVA may be used with a suitable machine learning method such as gradient-descent or mutual information based methods to provide a practical moderator discovery implementation. It is further contemplated that the EIGS may distinguish between categorical and non-categorical data together with the data type of each variable. The interactions and moderators component may further contain a Latent Variable Model (LVM) to enable the EIGS to relate observed data points (endogenous variables in causal models, also known as manifest variable) with latent variables (exogenous variables in causal models, also known as unobserved variables). Latent variable models may allow the EIGS to implement factor analysis methods, item response functions, multi-variate mixture models, latent class models (LCM) and latent class analysis (LCA).

The mediations component 1514 may contain information about the statistical and causal mediations applicable in the model 904, the EIGS and its components. Statistical and causal mediation models are stored in mediations component 1514 and may use a suitable machine learning process for the identification and creation of such mediation models, which may be serial or parallel in structure.

Statistical mediation models may refer to the statistical information held in hypotheses and concepts component 1511 and interactions and moderators component 1513, while causal mediation models may refer to the casual information held in hypotheses and concepts component 1511 and interactions and moderators component 1513 and the causal model held in hypotheses and concepts component 1511.

For both statistical and causal mediation models, mediation component 1514 may implement a practical way of explaining a subset of the information in the interactions and moderators component 1513 when additional variables, known as mediator variables (sometimes also known as a mediating, intermediary or intervening variable in literature), are necessary to be included to have a better quality candidate explanation 9102 or explanation 9141, for example, by clarifying the relationship between how independent variables influences the dependent variables in the model 904 and the EIGS and its components, via non-observable mediator variables. In an exemplary embodiment, the mediation component 1514 may provide practical implementations for mediation based on sequential conditional independence; estimation of effects under dynamic confounding and multiple mediators; partial identification based on sensitivity checks and bounds; experimental randomization of treatment and mediators; difference in differences approaches; multi-valued treatments; handling of different populations and outcomes; and handling of mismeasured mediators and missing outcomes.

The automated identification of mediator variables may provide a practical way of EIGS-based machine learning systems to identify cases of potential omitted-variable bias while also providing suggestions to the end users of the EIGS outputs on potentially missing data features in the input data to the models 904, or potentially missing elements from causal models in hypotheses and concepts component 1511, both when missing elements and data are Missing at Random (MAR) and also when they are Missing Not at Random (MNAR).

Practical implementations of mediation component 1514 may utilize a combination of the Baron and Kenny procedure, the Sobel test, the Preacher and Hayes bootstrap method, or other suitable methods to identify potential mediator variables automatically. It may be contemplated that mediator variables may be classified into either full or partial mediation classes, according to whether the discovered mediator variable can fully or partially account for the observed relationship between variables in the EIGS and its components.

Casual mediation models in mediation component 1514 may operate to identify the extent to which variables in the model 904 and the EIGS and its components participate in the transmission of change from the underlying causes to the observed effects. Causal mediation models in mediation component 1514 may utilize the appropriate causal logic system appropriate for the specific EIGS embodiment, with transmission and exchange of information with associations and assumptions component 1515, interventions component 1516 and counterfactuals component 1517. In a practical implementation, the indirect effect estimation methods of counterfactuals component 1517 can be used by mediation component 1514 to obtain a causal mediation result by calculating a counterfactual expression that estimates the natural indirect effect (NIE) in the absence of confounding. It is further contemplated that a practical implementation may utilize causal information to detect and handle extreme confounding situations correctly, such as Simpson's paradox, where apparent association between data features may appear to reverse when analyzed within each bucket, interval or group of a confounding variable.

In an exemplary medical application, when creating an explanation for the effect of a medical intervention, such as the administration of a treatment or drug or surgical procedure, on the actual or predicted patient outcome, the EIGS-based machine learning system should take into consideration possible interactions with other treatments, drugs, and so on. Adopting the well-known example in (Pearl, 2001) and (Richiardi, Bellocco, Zugna, 2013), where a medical intervention causes headaches in patients, who then subsequently take aspirin to cure the headaches, the effect of aspirin itself needs to be considered to control situations where the aspirin itself may be partially or fully causing the outcome, rather than the medical intervention. In this example, the aspirin is the mediator and data corresponding to the medical intervention, aspirin intake and outcome, together with any other relevant data, is available to the model(s) 904, which provide the necessary base statistics in the answer 9061 and the model explanation 9062. In this case, the justification 9063 may contain meta-information about why model explanation 9062 contains the base statistics that are being presented to model 904. The causal hypothesis about the medical intervention causing the outcome, while being mediated by aspirin intake is stored in hypothesis and concept component 1511 as a causal DAG. The EIGS may use counterfactual component 1517 to estimate the NIE of the medical intervention on the patient outcome by calculating the hypothetical counterfactual outcome for patients that had the medical intervention withheld (where the withholding statistics can be estimated by a joint combination of interaction and moderator component 1513 and mediation component 1514, especially if there is only a small number samples available in the data), and using hypothesis and concept component 1511, check if the patients would have had the same outcome had they been given as much aspirin as they would have taken if they had undergone the medical intervention. It may be contemplated that the NIE estimation may be performed on the full (population) sample available in the model 904 dataset or an adequate subset sample. In an exemplary embodiment, some form of Causal XNN (C-XNN) or a twin network structure may be used to implement such counterfactual analysis.

The EIGS-based system thus ensures that the explanation 9141 (and optionally, the interpretation 9142) clearly distinguishes between changes occurring in the patient's outcome due to aspirin intake induced by the medical intervention itself from changes occurring in the patient's outcome solely due to the medical intervention itself, regardless of aspirin intake.

If the dataset did not contain information about aspirin intake, the interactions component 1513 may identify that there is a variable missing between the medical intervention and the outcome, and subsequent versions of the model will be trained with new data that contains this feature (which then leads to the correct conclusion).

To further the example, suppose that a new improved medical intervention is created, as a result of the collaboration feedback with the EIGS-based system, that no longer induces headaches. The effect of this new improved medical intervention is that patients are no longer induced to change their aspirin intake apart from other reasons that are not related to the old medical intervention-induced headache. For example, the EIGS-based system may only have data from the old medical intervention. In this case, the EIGS may use counterfactual component 1517 to estimate the natural direct effect (NDE) of the medical intervention on patient outcome, together with additional data on aspirin intake for people in the population that were not exposed to the medical intervention. The additional data may either be already present in the dataset available to the model 904 or will have to be added to the EIGS-based system by fusing another model that does have the additional data, and using model fusion and link component 9064 to fuse such data seamlessly into the existing system.

Conversely, an exemplary EIGS-based system may also present a double-check in the explanation 9141 by considering the hypothetical situation where the medical intervention does not work when performed without aspirin intake. People in the population that take aspirin for reasons other than the medical intervention-induced headache may still experience an NDE related to the medical intervention. Those people in the population who take aspirin solely for the medical intervention-induced headache would have no NDE with the new updated medical intervention (since the headache side-effect is now eliminated). Additionally, the controlled direct effect (CDE) when aspirin intake is fixed at zero, would be the same in the two populations. This double-check allows for the EIGS-based machine learning system to produce a self-explanatory explanation that does not require further information. If the double-check procedure cannot be carried out due to lack of information that prevents the NIE, NDE, or CDE from being estimated, the evaluation component 1535 may add a follow-up, flag, or appropriate information in the explanation which may be used to inform the collaborative follow-up process followed by the consumers of the explanation 9141 and/or interpretation 9142.

Mediation and moderation may co-occur in exemplary explainable machine learning systems. EIGS-based systems allow for the mediation of moderation and the moderation of mediation using interaction and moderator component 1513 and mediation component 1514.

In mediated moderation, a moderating effect is mediated. Mediation component 1514 may handle mediated moderation by checking if the moderators identified by interaction and moderator component 1513 affects the relationship between the input (independent) variables and the output (dependent) variables according to the strength of the moderator itself. If such an effect is detected, mediation component 1514 may create a new mediated moderation path (associated with a new mediator variable) by applying the appropriate moderator effect via a new indirect path from the input (independent) variables to the output (dependent) variables via the newly created mediator variable.

In moderated mediation, one or more paths in a mediation model may be moderated. Mediation component 1514 handles moderated mediation by first establishing one or more mediation paths in conjunction with interaction and moderator component 1513. In an exemplary embodiment, the EIGS-based system may check if each mediation path is also moderated by different levels of another variable accessible to the model 904, the EIGS-based machine learning system, and its components.

An exemplary EIGS may use mediation component 1514 to automatically assign an automatically generated label to the resulting models, and also automatically generate a label for the mediation and moderation effects and variables according to their automatically discovered contributions.

An exemplary implementation of mediated moderation and moderated mediation in EIGS would adopt the methods outlined in (Muller, Judd, and Yzerbyt, 2005), (Preacher, Rucker, and Hayes, 2007) and (Kollenburg and Croon, 2011).

The associations and assumptions component 1515 may contain information pertaining to observations about data accessible to the model 904 and/or the EIGS, that may determine a combination of: (i.) statistical associations between sets of data variables, either directly or via some recursive process; (ii.) conditional probabilities between data variables that may or may not need causal information; (iii.) inferences and associations obtained from data using conditional expectation or similar methods; (iv.) answers to conditional probability sentences of the form $P(y|x)=p$, where the probability of an event $Y=y$, given that $X=x$ was observed, is equal to p, or a similar equivalent for the logic system being used in the EIGS in an exemplary embodiment; (v.) answers to exemplary scenario analysis of the form "What is X?", "How would observing X change the current beliefs in Y?" and similar types of questions.

For example, in a medical application, associations and assumptions component 1515 may be used to explain the implications and ramifications of medical symptoms on the currently predicted disease.

In an exemplary embodiment that uses cause-and-effect modelling in its implementation, associations and assumptions component 1515 may contain information corresponding to Rung 1 (Association) in Pearl's Ladder of Causation model (Pearl and Mackenzie, 2018).

An interventions component 1516 may contain information pertaining to observations about data accessible to the model 904 and/or the EIGS together with possible interventions and changes which may facilitate determining a combination of: (i.) conditional probabilities that distinguish between causal relationships from correlative relationships stored in associations and assumptions component 1515; (ii.) causal adjustments, multiple interventions; back-door identification and estimation methods; front-door identification and estimation methods; conditional interventions; covariate-specific effect identification and estimation methods; inverse probability weighting and estimation methods; confounder identification; suppressor variable identification; (iii.) causal inference obtained from using causal interventions or similar methods; (iv.) answers to conditional probability sentences of the form $P(y|do(x), z)=p$, which may be the probability of an event $Y=y$, given that an intervention that fixes the value of X to x and subsequently $Z=z$ was observed, set equal to p, where do( ) designates Pearl's do-expression or equivalent in the relevant causal logic system being used by the EIGS; (iv.) a similar equivalent for (iii.) in the logic system being used in the EIGS in an exemplary embodiment; (v.) answers to exemplary scenario analysis of the form "What if X?", "What would Y be if X is done?", "How can Y be made to happen?" and similar types of questions.

For example, in a medical application, intervention component 1516 may be used to explain how a patient's illness responds when a medical intervention is carried upon the patient in the form of a medical procedure such as the administration of a specific dose of medication, or carrying out a surgery, and so on.

In an exemplary embodiment that uses cause-and-effect modelling in its implementation, intervention component 1516 may contain information corresponding to Rung 2 (Intervention) in Pearl's Ladder of Causation model (Pearl and Mackenzie, 2018).

The counterfactuals component 1517 may contain information pertaining to observations about data accessible to the model 904 and/or the EIGS together with possible retrospective estimates, hypothetical interventions and hypothetical changes which may facilitate determining a combination of: (i.) hypothetical adjustments; hypothetical interventions; deterministic and non-deterministic counterfactual determination methods; abduction estimation methods; action estimation methods; prediction estimation methods; consequence estimation methods; attribution of causation estimation methods including but not limited to the estimation of probability of necessity, excess risk ratio, confounding factors; direct and indirect effect estimation methods including total effect (TE), controlled direct effect (CDE), natural direct effect (NDE) and natural indirect effect (NIE); (iii.) causal inference obtained from using causal counterfactuals or similar methods; (iv.) answers to conditional probability sentences of the form $P(y_x|x', y')=p$, providing that the probability of an event $Y=y$, had X been x, given that X was observed to be x' and Y to be y', is equal to p, or a similar equivalent in the logic system being used in the EIGS in an exemplary embodiment; (v.) answers to exemplary scenario analysis of the form "Why X?", "Was it X that caused Y?", "Would Y have been more likely to happen but for the existence of X?", questions that compare a world model to an alternative world model in which particular actions did not take place, and similar types of questions.

For example, in an exemplary medical application embodiment, counterfactual component 1517 may be used to explain if the administration of a specific dose of medication actually cured a patient's illness. In a further example, counterfactual component 1517 may be used to determine if a patient who died after receiving a specific dose of medication would have still died if that same specific dose of medication was not administered. In another further example, counterfactual component 1517 may be used to determine whether a patient who died during a surgical procedure that deviated from the standard process (as may be stored in the domain knowledge component 1524) would have still died if the surgical procedure fully followed the standard process.

In an exemplary embodiment that uses cause-and-effect modelling in its implementation, counterfactual component 1517 may contain information corresponding to Rung 3 (Counterfactuals) in Pearl's Ladder of Causation model (Pearl and Mackenzie, 2018).

It may be contemplated that counterfactual component 1517 may be integrated with a stationary or non-stationary stochastic process, such as a Markov process, Wiener process, Levy process, Gibbs sampling, Genetic Algorithms (GA), Particle Swarm Optimization (PSO), Monte Carlo process or other suitable process model to provide counterfactual capabilities from simulation results obtained by the process model.

It may be contemplated that counterfactual component 1517 may be integrated with a continuous or discrete dynamic systems model, phase space model, recurrent feedback control system model or other suitable process model incorporating cycles to provide counterfactual capabilities from simulation results obtained by a process model that incorporates cycles. It may be further contemplated that causal constraints may be used to augment and perturb data using possible transformations (such as rotation, translation, scaling, and so on) that are added to the augmented dataset unless contradicted by the observed data itself. Possible transformations may be found semi-automatically from the causal model structure. Symbolic knowledge may be used to further refine and filter what augmented data gets added to the dataset.

In an exemplary embodiment, components 1515, 1516 and 1517 may be used to form an ordered hierarchy of increasingly powerful causal implementation. For example, intervention component 1516 may use interventions together with associations from associations and assumptions component 1515 to determine answers 9061, model explanations 9062, candidate explanations 9102, explanations 9141, and justifications 9063. As a further example, counterfactual component 1517 may use counterfactuals together with interventions from intervention component 1516 and associations from associations and assumptions component 1515 to determine answers 9061, model explanations 9062, candidate explanations 9102, explanations 9141, and justifications 9063. Practical implementations may omit, simplify or merge components 1515, 1516 and 1517 depending on the need to handle cause-and-effect explanations for that particular embodiment.

The HKI component 1518 may contain information that enables human knowledge to be incorporated and injected into the EIGS in the form of machine-readable rules, logical sentences or any other suitable machine-readable format. It may be contemplated that a suitable interpretation process within HKI component 1518 may be used to translate natural language sentences to machine readable format for use by the EIGS. The EIGS may also use HKI component 1518 to incorporate feedback from human users in the explanation generation and interpretation process, and enable an element of collaboration between the machine learning system and human users in tandem with a combination of suitable interactive elements such as 1533, 1534, 1537, 1539, and 1544 or other suitable components within an exemplary EIGS.

The semiotics, taxonomical, and ontological component 1520 may include the metrics and dimensions 1521, taxonomies and ontologies 1522, semiotics 1523, and domain knowledge 1524 components.

The metrics and dimensions component 1521 may contain information about different systems of measurement needed to be utilized by the EIGS together with a combination of: (i.) underlying units and dimensions of measurement including but not limited to: (a.) a suitable distance function, (b.) differentiable manifold functions, (c.) translation, scale and rotational invariant metric functions, (d.) vector space metrics, (e.) multiset functions, and (f). topological functions; (ii.) relationships between the units and dimensions; (iii.) relationships with the base standard topological space used within EIGS including suitable maps, atlases, and transition maps; (iv.) relationships to the base standard metric system within EIGS for conversion purposes; and (v.) translation processes from machine readable formats to human readable formats and vice-versa.

In an exemplary embodiment, the EIGS may utilize the International System of Units (SI) or the United States customary system (USCS) as its base metric system together with a n-dimensional Euclidean space, a Minkowski space, or Riemann space as its base topological space, together with suitable maps and transforms allowing for the correct conversion and interpretation of units, metrics, metric spaces, dimensions and topological spaces by the EIGS and associated components and machine learning systems. The EIGS may also use topological transform functions to transform data from a T0 (Kolmogorov), T1 (Frechet), T2/T3/T4/T5/T6 (Hausdorff) and T3½ (Tychonoff) space into a T2/T3/T4/T5/T6 (Hausdorff) and T3½ (Tychonoff) space.

It may be contemplated that the EIGS may utilize semiotics, taxonomical, and ontological component 1520 to transform encoded information and units used by machine learning systems, such as one-hot encoding, or word vector embedding encodings to their original unencoded format and vice-versa. It also may be contemplated that the EIGS may utilize semiotics, taxonomical, and ontological component 1520 may implement any relevant gradient-descent and/or dynamic programming function needed by the machine learning system, such as back-propagation, in a verifiably correct manner that outputs results in the format needed as input by relevant subsequent machine learning systems.

The taxonomies and ontologies component 1522 may contain information about taxonomies and ontologies that are used by the EIGS to enhance information in the model 904 and all of the EIGS components while providing a practical solution to the standardization of information to all the EIGS outputs including but not limited to the answers 9061, model explanations 9062, candidate explanations 9102, explanations 9141, justifications 9063, interpretations 9142, explanation scaffolding 9101, and interpretation scaffolding 9111. An exemplary taxonomies and ontologies component 1522 may also contain transformations and mappings between taxonomies and ontologies to facilitate the conversion and translation of taxonomical and ontological data between different taxonomies and ontologies.

An exemplary taxonomies and ontologies component 1522 may also be used to link taxonomies and ontologies to causal models stored in hypotheses and concepts component 1511, thus combining the element of cause and effect analysis within the hierarchical structuring provided by taxonomies and ontologies. This causal model link may be used to improve the creation of casual models and improve the resulting quality of the explainable machine learning systems themselves in an iterative process of improvement.

It may be contemplated that taxonomies and ontologies component 1522 may be utilized in extending the features of the models 904 with taxonomy trees, networks and graphs and ontological trees, networks, graphs, hypergraphs and simplicial complexes. It may be further contemplated that taxonomies and ontologies component 1522 may be utilized in blending and fusing knowledge found in taxonomies and ontologies with human and machine-generated knowledge, which in an exemplary implementation may be transmitted via components HKI component 1518 and 904 respectively, and may also utilize a combination of components 1521, 1523, 1524, 1546, 1539, and 9800 in a practical fusion implementation.

In an exemplary embodiment, an EIGS-based system may use the OECD taxonomy of knowledge classes and the Suggested Upper Merged Ontology (SUMO) merged with the YAGO ontology (YAGO-SUMO) as default base taxonomies and ontologies that are then extended according to the specific application implementation.

For example, a medical application may utilize the Healthcare Provider Taxonomy Codes (HPTC) defined by the US National Uniform Claim Committee when interfacing with any Medicare compliant system. In this exemplary medical application, an MRI scan that forms part of the EIGS explanation and interpretation pipeline may be tagged with the National Provider Identifier (NPI) code "261QM1200X", which automatically identifies it as a Level III area of specialization. The EIGS-based machine learning system may automatically identify that the data should be grouped together with similar radiology data (which may be assigned a parent code of "261QR0200X") and has originated from a radiation therapy center with Medicare specialty code 74. In this exemplary medical application, the explainer 908, using the explanation scaffolding 9101, may determine that the MRI, together with other relevant explanatory information from the model 904, indicates that there may be a malignant lung cancer and uses the 2020 ICD-10-CM version of the International Statistical Classification of Diseases and Related Health Problems (ICD) taxonomy to assign it a diagnostic code of C34.90.

Figure 7:
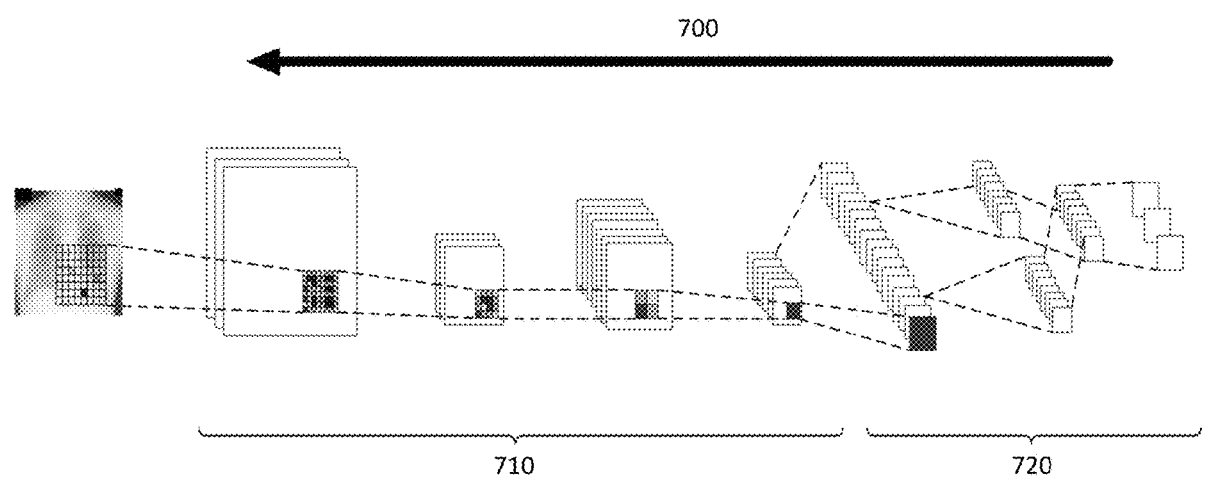
FIG. 7 is an exemplary embodiment of the Backmap.

The causal model in hypotheses and concepts component 1511 may fuse the MRI data with CT scan data via a CNN-XNN backmap 700, as illustrated in exemplary FIG. 7. Continuing the example, the model explanation of an analysis of bloodwork data via an XNN may indicate that there may be a level of uncertainty in the diagnosis that needs further follow-up. The system thus may assign an additional diagnostic code of D47.09, which indicates potential tumor cells of uncertain behavior. The diagnostic taxonomy codes may be used by the interpreter 912 to obtain a more certain interpretation of the results via the appropriate medical protocol transmitted in protocol context component 1548 and a plan of action transmitted by plan and question component 1537. The same diagnostic taxonomy codes may also be used by the system to create an appropriate reimbursement claim for medical health insurance purposes, as allowed by the filter 911, which ensures medical data privacy for the patient and healthcare provider.

Note that generic and explanation-oriented domain specific knowledge may be integrated in domain knowledge component 1524 while interpreter-oriented domain specific knowledge is integrated interpreter domain knowledge component 1546.

The semiotics component 1523 may contain information about the semantics and meaning of the information accessible via the model 904, the EIGS and its components together with a combination of: (i.) sign identification methods (kernels) and kernel labelling methods for different transmission modalities of symbols used by the EIGS-based system, including but not limited to tabular data, matrix data, multi-spectral images, 3D scans, videos, audio, text, speech, time series data, sequence data and other suitable data; (ii.) syntactical models that describe the formal properties and interrelation of the symbols used by the EIGS-based system with respect to their representation (surface) form and may optionally use component 1531 to store additional presentation data; (iii.) semantical models that describe the formal properties and interrelation of the symbols used by the EIGS-based system with respect to their meaning including links with taxonomies and ontologies 1522.

The domain knowledge component 1524 may contain information needed for the domain-specific application and embodiment of an EIGS-based system. The information in domain knowledge component 1524 may be used to enhance and structure the explanations 9141 and interpretations 9142 via the explanation scaffolding 9101 and the interpretation scaffolding 9111. Domain knowledge component 1524 may further utilize standard resources and machine learning models such as linguistic resources like WordNet and ImageNet, sequence-to-sequence and attention driven models, and other suitable resources and models that may be public and/or proprietary.

It may be contemplated that authorized third parties will be able to utilize component 1539 to read and write domain-specific knowledge in 1524 via an appropriate system that ensures data security and access control.

The scenarios, interaction, and presentation component 1530 may include the presentation data 1531, layouts and templates 1532, presentation state 1533, user model 1534, evaluation 1535, goals 1536, plans and questions 1537, actions 1538, third party data 1539, and world and environment model 9800 components.

The presentation data 1531 may contain information that the EIGS uses to generate the explanation and interpretation output in the desired format using the presentation layer, including but not limited to design configurations, presentation specific data and metadata, design schemes, multilingual models, and so on.

The layouts and templates 1532 may contain information that is used to layout output in the desired format and according to some prescribed layout and/or prescribed templated format, including output widgets.

The presentation state 1533 may contain information that is used to keep track of the state and history of the presentation layer, including but not limited to user interactions, clipboard data, user settings and preferences, notification settings, and so on.

The user model 1534 may contain a partial or full model of the system users themselves, regardless of whether they are human users or automated users. The user model 1534 may keep track of multiple system users, creating a user profile for each unique user and/or a group of users with similar characteristics. The user model 1534 may include, but is not limited to, a combination of the following items: personal information about the user, their interests, their skills and knowledge, their goals and plans, their preferences and dislikes about their behavior and interactions with the system, and other relevant user information. In an exemplary implementation, the user model may be an adaptive dynamic model that is regularly updated to take the current needs and goals of individual system users into account, while an adaptive stereotype based user model is used for groups of users with similar characteristics.

The justification 9063 in conjunction with the user model 1534 may be used by system users with different level of skillsets to understand the reasoning behind the model 904.

The evaluation component 1535 may contain information and methods for evaluating the quality, accuracy, precision, complexity, usefulness, satisfaction, fairness, bias, authority, precedence, effectiveness and other relevant attributes of an explanation and an interpretation, including but not limited to application-grounded, human-grounded, functionally-grounded methods. The evaluation component 1535 may also contain suitable evaluation methods to determine the degree of achievement of goals, plans, actions and question-answers such as a reinforcement learning based implementation or any other suitable implementation. The evaluation component 1535 may also contain suitable evaluation methods that evaluate various criteria about the EIGS system and its components. The evaluation component 1535 may also generate audit logs containing information about the evaluations performed and optionally transmit this audit log to the third-party data component 1539 in a secure and tamper-proof manner.

An exemplary evaluation component 1535 may also implement statistical tests to determine the quality of model fits to the data, especially for the associations and assumptions part in hypothetical and causal component 1510, with typical tests using the chi-squared test, root mean square error of approximation (RMSEA), comparative fit index (CFI), standardized root mean square residual (SRMR), and other suitable tests. Evaluation component 1535 may also implement causal tests to determine the quality of the casual model fits to the causal model and to the data, especially for the interventions and counterfactuals parts in hypothetical and causal component 1510.

The goal component 1536 may contain information about the system user goals that may drive plans and questions by the plan and question component 1537 and ultimately lead to actions in action component 1538. Goals may be classified into a number of primary and secondary goals, where primary goals drive plans and actions and secondary goals are derivatives of primary goals. Furthermore, both primary and secondary goals may conflict with one or more goals and can change over time. System users may be acting upon multiple goals at a time, depending on current circumstances, which may be stored in the presentation state 1533 and user model 1534.

The plans and questions component 1537 may contain information and methods to represent and execute plans and at handling dialogue, interaction and question-answering by the EIKS. Plans are classified as strategic plans or tactical plans. Strategic plans indicate to the EIKS-based system what should be accomplished and may be generic in nature. Tactical plans indicate to the EIKS-based system how the strategic plans will be accomplished and may be specific in nature. The question-answering methods handle situations where a degree of interactivity, interaction and interrogation are needed, for example, in an interactive medical diagnostic application or a chatbot type of application. Questions may be classified by plan and question component 1537 as being either of a closed or open form, and their type as being factual, list-based, definition-based, how-type, why-type, hypothetical and counterfactual-type, semantically constrained-type, multi-lingual and other suitable question classification categories. Each answer to a question may be iteratively added via the exemplary pipeline in FIG. 2, refining the answer 9061, model explanation 9062 and optional justification 9063 and subsequently all other components and outputs further down the pipeline. An exemplary plan and question component 1537 may use a multi-modal question-answering implementation in conjunction with components 1531, 1532 and 1533 to use multiple modalities of system user input to enter questions and answer them in different modalities, including but not limited to text, images, 3D data, tabular data, video, speech, audio, haptic information, time series, sequence data and other suitable modalities supported by the model 904 and the EIKS-based system implementation.

The actions component 1538 may contain information about the allowed actions and an action selection policy that utilizes a decision-making strategy and information from interaction and presentation component 1530 and other components within the EIGS-based system to select the next action to perform, when appropriate. In an exemplary embodiment, a suitable explainable system, such as an XRL agent, may be used to implement explainable actions, allowing full interpretability and explainability of an exemplary system throughout. In a further exemplary embodiment, an action execution oriented system such as a Robotic Process Automation (RPA) system or an ERP system may also be used to implement explainable actions. Action component 1538 may adopt a combination of: (i.) symbolic approaches, (ii.) distributed approaches with or without an attention model, and (iii.) dynamic or reactive approaches, to implement the action selection policy and the decision-making strategy. The application requirements may guide the implementation and embodiment choices. For example, in a medical diagnosis application, a fully blown symbolic approach may be adopted to give the best in-depth explanations and interpretation, while in a surgical robot embodiment, a dynamic or reactive approach may be adopted to certain processes that require fast, time-critical actions, such as suturing wounds or closing an unexpected rupture that may use a combination of software and dedicated hardware embodiment to achieve flexibility in updating the surgical robot while ensuring fast and reliable execution of real-time or quasi-real-time time critical or emergency surgical procedures.

The actions component 1538 may allow the EIGS to output actionable explanations and/or interpretations, containing a mixture of explanatory information together with actionable recommendations that are backed up with the appropriate explanations, interpretations and/or justifications.

The actions component 1538 may also keep a suitable audit log of actions performed by the EIGS-based system and optionally transmit this audit log to the third-party data component 1539 in a secure and tamper-proof manner.

Third-party data 1539 may contain any relevant data from a third-party source that may extend the EIGS via relevant plugins, modules, apps, expansion circuits and other suitable methods of extending the EIGS depending on the application embodiment. Approved third parties can access various aspects of the explanation scaffolding 9101 and the interpretation scaffolding 9111 using an appropriate data security model that protects integrity, data privacy and other relevant constraints while simultaneously allowing approved third parties to transform and enhance the resulting explanations 9141 and interpretations 9142 as part of the EIGS pipeline. The explanation filter interpretation (EFI) model allows for approved third parties to be seamlessly integrated in each of the main steps of the pipeline, for example, at points 908, 911 and 912.

In an exemplary embodiment, an EIGS may be used as the basis of a practical data privacy preserving AI system implementation. Data privacy may be violated intentionally or unintentionally by AI systems in a number of scenarios, with some examples being: (i.) personal data from training datasets unintentionally incorporated in AI models; (ii.) personal data can be re-extracted or re-created by analyzing the model answers repeatedly; (iii.) personal data of certain uniquely identifiable groups may end up at a higher risk of identification; (iv.) model inversion and membership inference techniques, that can associate model data via a unique key or signature; or (v.) other sources of information, such as public data sources, can be combined with private information to re-create or otherwise identify private information. The main data privacy preserving solutions for AI can be classified under four categories: (i.) differential privacy; (ii.) secure multi-party computation; (iii.) federated learning; and (iv.) homomorphic encryption. Exemplary embodiments of EIGS may enable practical implementations under all four categories.

In privacy preserving solution (i.), differential privacy, the introduction of noise in the training data or some other suitable means of obfuscation, may be used to generate a controllable amount of privacy through a noise factor or ratio, in the explainable AI models within an EIGS. Exemplary embodiments of EIGS that utilize explainable models that have selective deletion and editing capabilities, such as XNNs, can add such noise selectively according to a data privacy model. The audit trail functions of an EIGS can also be used to detect an anti-obfuscation attack and generate noisy information on purpose to defeat such an attack to prevent private information from being identified through repeat querying of the same data row.

In privacy preserving solution (ii.), secure multi-party computation (SMPC) may be used to obtain a correct answer while concealing partial information about data yet simultaneously computing the answer using data from many sources. EIGS can extend SMPC protocols to cover explanation generation apart from answer output. Exemplary embodiments of EIGS may utilize explainable models that are easy to apply to SMPC implementations. Additionally, an EIGS can be analyzed and tested formally for security and trust building purposes without revealing any secrets. An end-to-end hardware implementation of an EIGS with a secure enclave will be rather resilient to most forms of data attacks. It is further contemplated that selected parts of an EIGS will be implemented in such an enclave.

In privacy preserving solution (iii.), federated learning, an exemplary EIGS may utilized several explainable models that have been jointly trained across various decentralized devices that hold only local data samples.

In privacy preserving solution (iv.), homomorphic encryption, or homomorphic computing, an exemplary EIGS may utilize a protocol such as the Cheon-Kim-Kim-Song (CKKS) protocol, Brakerski-Gentry-Vaikuntanathan (BGV), Brakerski/Fan-Vercauteren (BFV), or the FHEW Fully Homomorphic Encryption protocol (sometimes given the bacronym "Fastest Homomorphic Encryption in the West"), to allow computation on encrypted data without either decrypting the data and also, optionally, using encrypted explainable models.

The world and environment model 9800 may contain models of the environment with which the EIGS-based system may interact together with models of the world beyond the immediate environment that may be needed to explain and interpret actions in a correct manner, for example, by incorporating physics and illumination models. The world and environment model 9800 may also have support for behavioral models, behavioral model hierarchies, action triggers and/or feedback loops.

FIG. 8 illustrates an exemplary embodiment of an explanation scaffolding structure. Exemplary embodiments may merge some or all of the components and sub-components together or emit them completely. In a modification example, components 9064, 1510, 1520, and 1530 may be omitted completely in a basic implementation. In a further modification example, the sub-components 1531, 1532, and 1533 of the scenarios, interaction, and presentation component 1530 may be merged into a single component without significant loss of functionality for many practical implementations.

In an alternative embodiment, the third-party data 1539 or the world and environment model 9800 may be implemented separately from the explanation scaffolding and input to the explainer and/or a system implementing the EFI model as an independent component.

EIGS generated explanations 9141 and/or interpretations 9142 can contain a number of user-centric explanation types that are suited towards the system user or a group of system users as indicated by 1534. The EIGS classifies user-centric explanation types as follows: (i.) how-type explanations that represent how the model 904 works, via model interpretability and optional justification 9063; (ii.) why-type explanations that explain why a particular explanation and/or prediction has been output for the particular input query 902, with either a model agnostic or model dependent explanation that may involve cause-and-effect explanation chains; (iii.) why-not (contrastive) explanations that explain why a specific output was not in the output of the EIGS system and explain the reasons for differences between a model prediction and the system user expected outcome; (iv.) what-if explanations that explain how different inputs affect the model output and may be either automatically recommended by the EIGS or be chosen interactively for exploration through plan and question component 1537 or interactive context component 1544; (v.) how-to (counterfactual) explanations that explain hypothetical adjustments to the input or to the model that would result in a different output and may allow the system user to explore different hypothetical scenarios interactively; (vi.) what-else explanations (explanation by example) which enhance explanations with similar instances of input that generate identical or similar outputs from the model.

The explanation 9141 may contain multiple detail levels that can be output individually or together according to some selection criteria. The multiple detail levels may be achieved via some progressive addition, subtraction or other suitable transformation. Multiple detail levels may also be in the form of a hierarchical structure, network or graph structure. Multiple detail levels may also be in a form suitable to the presentation information given in 1530 and its sub-components, for example, in case of image data, there may be images at different resolutions, overview and key images, and other suitable detail pertinent to the embodiment of the EIGS. Multiple detail levels may also be broadly classified by the EIGS as a summary, detailed, or conclusive type.

Additional detail may be added as needed. For example, white-box explainable models can output advanced bias information, bias explanations and strength/weakness detection information at multiple detail levels, which may be incorporated within the model explanation 9062 and optionally in the answer 9061 and/or its justification 9063. It is further contemplated that the EIGS may utilize a suitable user model to determine the suitable level of detail, together with a skill acquisition model such as the Dreyfus model, Argyris action model or other suitable model.

The explanation 9141 may contain multiple types of explanations that can be output individually or together according to some selection criteria. Different types of explanations may include a combination of: (i.) local explanations that are concerned about a particular sub-set of the explanation domain and information domain being used by the underlying machine learning system such as the model 904; (ii.) global explanations that are concerned about the entire explanation domain and information domain being used by the underlying machine learning system such as the model 904; (iii.) post-hoc and ante-hoc explanations as generated by the grey-box or white-box machine learning system such as the model 904; (iv.) user type and group personalized explanations that have been transformed and filtered to cater to the needs of a particular type of user or group or industry, for example, using information that is stored in the user model 1534; (v.) user specific and fully personalized explanations that have been transformed and filtered to cater to the needs of a particular user, for example, using information that is stored in the user model 1534; and (vi.) summary, detailed and conclusive types of explanations.

Different types of explanations may also result from the different output formats and layouts. Multiple output formats may be stored within the same explanation scaffolding. For example, an advanced medical application may store multi-spectral images including MRI scans, X-Rays, UV, IR and visible light images, together with ultrasound scans and audio recordings, 3D computed tomography data, 3D positron emission tomography data, time series electrocardiogram data, structured health measurement data such as timestamped blood pressure readings and bloodwork results, and templated interpretation text data from relevant specialists. An exemplary EIGS may combine and fuse the answers, model explanations, and justifications arising from one or more models and uses the model fusion and links 9064 to keep track of the provenance and fusion adjustments needed to present a coherent explanation and subsequent interpretation. An exemplary EIGS may also utilize various widgets and output formats to explain particular details in an explanation output, including but not limited to structured text templates, funnels, tree maps, graphs, relational dependency networks, feature maps, dependency graphs, heatmaps, Shapley values, path traces, confusion matrices, strength and weakness matrices, confidence intervals, case based examples, prototypes, exemplars, nearest neighbours, proximate neighbours, rules, text, images, infographics, diagrams, box-and-whisker plots, candlestick charts, geospatial maps, highlight tables, radial trees, cohort diagrams, dendograms, timelines, root cause analysis/fishbone diagrams, Petri nets, activity diagrams, UML diagrams, cord diagram, Manhattan plots, and other suitable visualizations and output elements. It is further contemplated that a practical EIGS implementation may utilize an XRL agent to create, modify and refine the explanation output, including in situations where a particular strategy needs to be recommended to change the outcome of a particular prediction. It is further contemplated that the EIGS may utilize an XGAN and/or XAED to generate, refine and modify explanation output elements.

A further exemplary embodiment of hypothetical and causal component 1510 allows for different types of confirmatory factor analysis (CFA), including support for different alternative estimation strategies, such as Maximum Likelihood, Polychoric Correlations, Liability Threshold models and other suitable estimation models. CFA type exemplary embodiments may utilize the hypotheses information, together with other suitable information in the explanation scaffolding, like the HKI component and prior assumptions to allow constraints on particular features to be modeled, checked, verified and utilized as part of the explanation scaffolding.

A further embodiment of hypothetical and causal component 1510 allows for different types of exploratory factor analysis (EFA), including support for induction of different hypotheses, automated and semi-automated model discovery, supervised and unsupervised model optimization, and bootstrapping of constraints on particular features to be modeled, checked, verified and utilized as part of the explanation scaffolding. Continuing with the example, an AutoXAI system may use Multiple Objective Optimization (MOO) to perform model discovery and optimization within the EIGS.

EFA and CFA embodiments may be combined together in parallel or in sequence. An exemplary application of a sequential process may use an initial EFA to discover a preliminary hypothesis or set of hypotheses, which are then refined and confirmed by an exemplary CFA. Another exemplary sequential process application may use a CFA, which may conditionally trigger an exemplary EFA if the evaluation results in 1530 are not of good enough quality as specified in hypothetical and causal component 1510. An exemplary parallel process application may use multiple EFAs or an ensemble-like system of parallel EFAs that discover and predict different plausible hypotheses and scenarios which are then examined by an automated system or a human user and possibly selected for further processing.

In an exemplary embodiment, the EIGS may utilize conditional rules in the form of IF-conditions in order to activate one or more rules or one or more partitions. The conditional evaluation output may be binary, multi-class or a real number using a Type 1 or Type 2 fuzzy logic system or similar system. It is further contemplated that the conditional evaluation output could be with reference to at least one of an associated tree, graph or hypergraph structure, a simplicial complex, a taxonomy, an ontology or causal model. The conditions themselves may be static or dynamic, and may be discovered either through an internal EIGS process, or a suitable external process, or through a connected explainable model, or a connected EIGS.

In another exemplary embodiment, an EIGS may be implemented using a quantum processing system. It is contemplated that such a Quantum EIGS will have characteristics that are similar to an EIGS implemented on a classical non-quantum processing system with the addition of quantum specific extensions. For example, such an extension may allow for the specification of quantum annealing effects and their correct interpretation. In another example, an extension may allow for the correct interpretation of multiple qubit states, qubit basis states, mixed states, Ancilla bits, and other relevant quantum effects due to entanglement and/or decoherence. In another example, an extension may allow for the introduction of quantum logic specific operators and/or hardware logic gates within the Quantum EIGS logic, such as quantum CNOT, CSWAP, XX, YY, ZZ gates, Pauli gates, Hadamard gates, Toffoli gates and other relevant quantum logic operations that may be combined serially or in parallel. Furthering these examples, such quantum specific extensions may be implemented in various parts of the EIGS system, for example by having quantum extended versions of conditions, events, triggers, actions, input processing and output processing. It is further contemplated that such Quantum EIGS systems may take advantage of quantum effects, for example, to execute multiple actions, or evaluate multiple conditions, or evaluate large systems of constraints in significantly fewer processing steps needed than possible on a classic processing implementation.

An exemplary EIGS, model 904, explainer 908, filter 911, interpreter 912, explanation scaffolding 9101, interpretation scaffolding 9111, explanation 9141, interpretation 9142 and all their relevant sub-components may utilize a combination of classical and non-classical logic systems such as Boolean logic, first order logic, second order logic, propositional logic, predicate logic, modal logic, probabilistic logic, many-valued logic, fuzzy logic, intuitionistic logic, non-monotonic logic, non-reflexive logic, quantum logic, paraconsistent logic or other suitable type of logical system for the expression of logical or similar statements within the EIGS and all of its components, inputs and outputs. The EIGS its components may further utilize a combination of deductive, inductive, abductive, functional, concurrent, agent-based and metaphoric reasoning for the expression of logical arguments or similar statements within the EIGS and all of its components, inputs and outputs.

Interpretation scaffolding may be used to provide a practical embodiment of interpretations and interpretation information for explainable machine learning systems and other automated systems.

FIG. 9 illustrates an exemplary structure for an interpretation scaffolding 9111. The interpretation scaffolding 9111 may be structured into three main components, the explanation and interpretation scenario component 9112, the framing, protocol and contextual component 1540, and the interpretation model component 1550.

The explanation and interpretation scenario component 9112 may include a suitable version of the explanation scaffolding 9101, such as the one illustrated in FIG. 8, together with an interpretation scenario 9113. The interpretation scenario 9113 may be used to aid in the creation and configuration of an interpretation brief 1547. The interpretation scenario 9113 may optionally influence the behavior of the selection model 1553.

The framing, protocol and contextual component 1540 may include the interpretation framing 1541, interpretation rules and procedures 1542, protocol context 1548, interpretation brief 1547, interpretation templates 1545, interpreter domain knowledge 1546, interpreter beliefs 1543 and interactive context 1544 components.

The interpretation framing 1541 may supply information on how the interpretation may be framed, including any specific models, representations, and simplifications that should be applied by the interpreter.

The interpretation rules and procedures 1542 may supply rules that govern how the interpretation should be created, how disambiguation should be carried out, and what procedures are applicable for the current interpretation.

The protocol context 1548 may contain information about the protocol to be used when processing the explanation scaffolding 9101, and how the different system agents components should communicate. In implementations that require an iterative interrogation sequence of some sort, such as a sequence of questions and answers, that may also involve further queries to the explainable machine learning system, the protocol context 1548 may also contain information about how the interrogation protocol should be implemented.

For example, in a regulated industry such as medicine, certain medical procedures mandate the use of approved medical protocols and processes. In a practical embodiment of a medical diagnosis system, the Protocol Context 1548 may contain details on what information to collect about a patient, in what format and manner it should be collected, and what processes should be applied to any hardware that is being controlled by the system and in what order.

The interactive context 1544 may contain information about interactive and iterative processes that need to be tracked during the interpretation process. The interactive context component 1544 may also generate audit logs containing information about the interactive and iterative processes performed and optionally transmit this audit log to the third-party data component 1539 in a secure and tamper-proof manner.

The interpretation brief 1547 may supply information to the interpreter on how the interpretation is to be carried out. The interpretation brief may be an output of the filters in the EFI model, which is illustrated in FIG. 10.

The interpretation templates 1545 may supply information to the interpreter on how the interpretation output and results are to be structured. This is distinct from the presentation information in the scenarios, interaction and presentation component 1530 within the explanation scaffolding 9101, which is utilized to create a human and machine-readable version of the output as desired for both the explanation and its interpretation. There may be multiple interpretation templates whose selection is governed by the interpretation scenario.

For example, in a medical application, the interpretation templates for a particular medical scan may contain the mandatory and optional pieces of information that are needed as part of the interpretation, together with details about their format, confidence intervals, significance rules, red flagging rules and other suitable instructions.

The interpreter domain knowledge 1546 may contain additional domain-specific knowledge that is available to all interpreters. The information in the interpreter domain knowledge 1546 may be used to enhance and structure the interpretations 9142 via the interpretation scaffolding 9111. The interpreter domain knowledge component 1546 together with the third party data component 1539 within the explanation scaffolding 9101 may enable a practical method to extend the interpreter behavior via third party implementations, plugins, modules and other similar extension methods suitable for the application embodiment and to read and write interpreter domain-specific knowledge in the interpreter domain knowledge component 1546 via an appropriate system that ensures data security and access control.

The interpreter beliefs 1543 may contain a combination of domain-specific and domain-independent knowledge, together with scenario-specific information that is available to one or more interpreters. Each interpreter may share a subset of its interpreter beliefs with other parts of the system or may keep a subset private and thus effectively hidden from the rest of the system.

The interpretation model component 1550 may include the scenario model 1551, interpretation model 1552, selection model 1553 and conflict resolver 1554 components.

The scenario model 1551 may contain scenario-specific details about the current scenario that are needed by the interpreter in addition to the information available in interpretation scenario component 9112 and its sub-components, such as the explanation scaffolding component 9101 and interpretation scenario component 9113.

The interpretation model 1552 may contain a combination of domain-specific, scenario-specific and interpretation brief specific details that are needed by the interpreter in addition to the information available in interpretation scenario component 9112 and its sub-components.

The selection model 1553 may contain details on how the selection process will determine how the ranked and scored interpretations that may result from the interpreter or ensemble of interpreters be filtered and transformed into a final set of selected interpretation(s).

The conflict resolver 1554 may contain a combination of domain-specific and domain-independent knowledge, together with scenario-specific and interpretation brief specific information on how conflicts during the interpretation process and how conflicts between a combination of interpreters and filters should be resolved. The conflict resolver 1554 may additionally contain action triggers that are activated when the current conflict cannot be resolved within the current interpretation process. The action triggers may involve further calls to the explainable machine learning system that created the input or to other appropriate automated systems. It may be contemplated that some action triggers may require human intervention when the automated system determines that a situation has been encountered that cannot be handled in an automatic fashion or where it may be dangerous or otherwise problematic to do so.

Referring now to FIG. 9, FIG. 9 illustrates an exemplary embodiment of an interpretation scaffolding. Practical embodiments may merge some or all of the components and sub-components together or emit them completely. In an exemplary embodiment, the framing, protocol and contextual component 1540 may be omitted completely in a simpler implementation. In a further modification example, the sub-components 1551, 1552, 1553 and 1554 of the interpretation model component 1550 may be merged into a single component without loss of functionality for many practical implementations.

In an alternative embodiment, the explanation scaffolding 9101 may be implemented separately from the interpretation scaffolding and input to the interpreter and/or a system implementing the EFI model as an independent component.

An exemplary EFI model may present a practical solution of how an interpretation 9142 may be obtained from an exemplary EIGS pipeline such as the one illustrated in FIG. 2, or a suitable alternative.

FIG. 10 illustrates an exemplary implementation of an EFI model. An EFI model may use components 1541, 1548, 1542, 9113, 1553, 1554, 1547, 1545, 1546, 1544 and 1543 from the interpretation scaffolding 9111. The EFI model may add an ensemble of filters 9200, an ensemble of interpreters 9300, together with some exemplary processes, such as: intra-filter agreement process 9210, inter-filter agreement process 9220, intra-interpreter agreement process 9310, inter-interpreter agreement process 9320, and the selection process 9340. The inter-interpreter agreement process 9320 may output an intermediate output called the ranked interpretations 9330, while the selection process 9340 outputs the final output of the EFI model itself, the selected interpretations 9142. An exemplary embodiment of the EFI model may utilize a workflow system for a practical implementation.

The EFI model may use the explanation 9141 available via the explanation scaffolding 9101 and/or the explainer 908 as its starting input.

The explanation 9141 may be input to the filters 9200 together with the interpretation framing 1541, protocol context 1548, interpretation rules and procedures 1542, and the interpretation scenario 9113. The interpretation scenario exchanges information with the selection model 1553.

The filters F1 . . . Fn may themselves be a simple or complex transformation function, or an explainable machine learning system. An exemplary embodiment of a filter may thus be an induced XAI model, XNN, XTT, XRL, XMN, XSN or INN or suitable white-box or grey-box model equivalent. The filters may also be implemented as a distributed explainable machine learning system such as a distributed XNN. The filters may also utilize different components in the EIGS to implement advanced behavior. For example, a filter may utilize components 1515, 1516 and 1517 in the explanation scaffolding 9101 to implement cause-and-effect analysis.

Each filter F1 . . . Fn may have an associated intra-filter agreement process 9210 that provides agreement and resolution within the filter itself.

The filters 9200 may have an inter-filter agreement process 9220 that provides agreement and resolution across all the filters. The EFI model may use appropriate methods such as the Cohen Kappa, Fleiss Kappa, or Krippendorff Alpha statistic to fuse multiple outputs from the filters 9200 together.

An output of an exemplary inter-filter agreement process 9220 may be the interpretation brief 1547. The interpretation brief 1574 and the interpretation templates 1545 may be fed as input to the interpreters 9300, together with the interpretation model 1552, conflict resolver 1554, scenario model 1551, interpreter domain knowledge 1546. Additionally, for interpretations that require an interactive or iterative type of process, the interpreters may also use the interactive context 1544.

The interpreters I1 . . . Im may themselves be a simple or complex transformation function, or an explainable machine learning system in their own right. An exemplary embodiment of a filter may thus be an induced XAI model, XNN, XTT, XRL, XMN, XSN or INN or suitable white-box or grey-box model equivalent. The interpreters may also be implemented as a distributed explainable machine learning system such as a distributed XNN.

Each interpreter I1 . . . Im may have an associated intra-interpreter agreement process 9310 that provides agreement and resolution within the interpreter itself. Each interpreter may also have an associated interpreter belief component 1543, which may have a shared and private area for the interpreters. Each interpreter may have its own private area allocated to it in belief component 1543, while a shared area allows the interpreters to communicate and exchange beliefs within a subset of all other interpreters.

The interpreters 9300 may have an inter-interpreter agreement process 9320 that provides agreement and resolution for all the filters. The EFI model may use appropriate methods such as the Cohen Kappa, Fleiss Kappa, or Krippendorff Alpha statistic to fuse multiple outputs from the interpreters 9300 together.

The inter-interpreter agreement process 9320 may output the ranked interpretations 9330, which is then input to the selection process 9340 together with the selection model 1553. The selection process 9340 may implement a final form of selection and/or transformation of the ranked interpretations 9330 to produce the final output of the EFI model, the selected interpretation(s) 9142.

In an exemplary embodiment, the selected interpretation(s) 9142 may be utilized as input to further automated systems and/or human users.

An exemplary EFI model may be illustrated in FIG. 10. Exemplary embodiments may merge some or all of the components and sub-components together or emit them completely. In a modification example, the components 1541, 1548, 1542 and 9113 may be merged into a single component without significant loss of functionality for many practical implementations. In a further modification example, the intra-interpreter agreement process 9310 may be completely omitted. In an alternative embodiment, the filters 9200 may be implemented with a trivial function that simply sets a default catch-all interpretation brief 1547. In another alternative embodiment, the filters 9200 may be completely omitted from the implementation, especially in embodiments where there is no need for filtering or that have significant time and resource constraints such as dedicated hardware applications.

It may be contemplated that in a feedback type of process, a feedback loop between the selected interpretation(s) 9142 back to the interpreters 9300 and/or the filters 9200 may exist. A feedback loop may be useful when the results of the interpretation process are utilized in an iterative fashion when a sequence of interpretations are needed.

Note that in a feedback loop iteration, the interpreters 9300 and/or filters 9200 do not necessarily need to remain the same in subsequent passes. The EFI model implementation thus may allow for a variety of a combination of different systems, agents and models to be used in both the filtering and interpretation processes.

It is contemplated that the Candidate Explanation 9102, generated by the Explanation Scaffolding 9101, and/or the filtered version of the Candidate Explanation 9102 generated by the Interpretation Scaffolding 9111, may be used to create a transformed version of the Candidate Explanation in the form of an Interpretation 9142. Such Interpretation may represent a Transformed Explanation or Interpretation Representation of the Input Query 902. Such Transformed Explanation or Interpretation Representation may be used in another Explainable and/or Interpretable Model, as part of its input. Such a Model may be used to learn and predict Explanations and/or Interpretations and use such predictions to improve the quality of the EIGS output and help identify bias, strengths and weaknesses in the output results. It is further contemplated that a sequence of Explanation and/or Interpretation predictions and/or a sequence of Explanation and/or Interpretation representations may be used by the EIGS to analyze the flow of the Explanation and/or Interpretation values and features over time. Such flow may be incorporated in a behavioral model BM, to enable particular changes in values or features in the Explanation and/or Interpretation to be monitored and optionally acted upon. In an exemplary embodiment, a conditional constraint may be set on the gradient of the flow of the feature stress, in a medical treatment application. The trigger of such conditional constraint would activate an action to stop the current ongoing treatment of the patient. Behavioral models may also be used to both act as input sources in the generation of an explanation and also to consume the output of the resulting output explanation. Behavioral models may also be used to guarantee and assure behavior of an EIGS.

An exemplary embodiment in a medical diagnosis application of the EFI model with such a feedback loop may include a medical scenario interpretation that recommends some particular medical intervention, output collaboratively by a medical diagnosis system or suitable hardware. When the recommended medical intervention is flagged for review and re-interpretation by an independent medical governance board or a different system or model, a feedback loop may be utilized to link the subsequent interpretation step with the current interpretation step.

It may be further contemplated that the interpretation templates 1545 are optionally a product of some or all components in the explanation scaffolding 9101. In an exemplary embodiment, the interpretation templates 1545 may be formulated according to the specifications given by the goals 1536, plans and questions 1537 and actions 1538 components.

Interpretation bias can be modeled using the EFI model, which maintains a causal DAG that attempts to model the inherent interpretation bias that is most often involved in the production of an interpretation from an explanation. The EIGS EFI model may recognize and model the multiple types of interpretation bias, such as: framing bias, protocol bias, interpretation rules bias (societal bias), interpretation scenario bias, filter bias, interpretation template bias, interpretation brief bias, interpreter bias, interpreter beliefs bias, shifting interpreter bias, interpreter error bias, and selection model bias.

Framing bias, protocol bias, interpretation rules bias (societal bias) and interpretation scenario bias may arise from bias in the interpretation framing component 1541, protocol context component 1548, interpretation rules and procedures component 1542, and interpretation scenario 9113 respectively. The EIGS may model biases as exogenous variables.

Filter bias can arise from the hidden and known biases of each filter F1 . . . Fn in the EFI model filters 9200. The known biases of each filter may be modeled in the EIGS as an endogenous variable, while the hidden biases of each filter may be modeled using an exogenous variable. A combined bias estimate for all filters may also be modeled.

The interpretation template 1545 itself may give rise to an interpretation template bias, which is a form of selection bias due to the questions that are being asked in the template and what information is being sought (and what is being ignored) for interpretation. An exemplary EIGS may model interpretation bias as endogenous variables.

Interpretation brief bias may be modeled in the EIGS as a dependent variable that depends on the filter bias and the interpretation template bias. Interpreter bias may arise from the hidden and known biases of each interpreter I1 . . . Im in the EFI model interpreters 9300. The known biases of each interpreter may be modeled in the EIGS as an endogenous variable, while the hidden biases of each interpreter may be modeled using an exogenous variable. A combined bias estimate for all interpreters may also be modeled.

Interpreter beliefs bias can arise from the hidden and known biases of each interpreter I1 . . . Im beliefs in the EFI model interpreters 9300. The known biases of each interpreter beliefs may be modeled in the EIGS as an endogenous variable, while the hidden biases of each interpreter beliefs may be modeled using an exogenous variable. A combined bias estimate for all interpreter beliefs may also be modeled.

In an interactive interpretation scenario, the interpreter bias may shift and evolve as the interpretation iteration progresses. The EIGS may model the shifting interpreter bias using a Markov Process or any suitable deterministic process equivalent.

The EIGS may further model interpreter error bias as an exogenous variable to model the fact that the interpreter may not always follow the interpreter brief and the fact may be hidden to the EIGS and the system user.

The selection model may also give rise to selection model bias, which may be modeled by the EIGS as an endogenous variable. The selection model may be a white-box model and hence amenable to bias detection and correction methods.

An exemplary embodiment may allow for explanations and interpretations to be personalized and/or be transformed to incorporate situation-specific scenarios, building up on the earlier steps, in a linear or non-linear fashion, in a typical EIGS pipeline or workflow such as the exemplary embodiment illustrated in FIG. 2 or a suitable alternative. It is further contemplated that the process in FIG. 2 is implemented and/or incorporated within a workflow system.

The explanation scaffolding 9101 can be further personalized and/or be transformed to incorporate situation-specific scenarios with the utilization of a combination of the explanation model component 906, hypothetical and causal component 1510, semiotics, taxonomical and ontological component 1520, and the scenarios, interaction and presentation component 1530, and any or all of their sub-components.

Interpretations may be personalized and/or be transformed to incorporate situation-specific scenarios and other information in a similar manner to explanations. The interpretation scaffolding 9111 can be further personalized and/or be transformed to incorporate situation-specific scenarios with the utilization of a combination of the explanation scaffolding 9101, interpretation scenario 9113, framing, protocol and contextual component 1540, and the interpretation model component 1550, and any or all of their sub-components.

In an exemplary embodiment, explanations may be personalized and/or transformed to cater to: (i.) various user characteristics as specified in a user model 1534; (ii.) to incorporate and meet various goals, plans, milestones, evaluation criteria and constraints specified in evaluation 1535, goals 1536, plans and questions 1537, and actions 1538; (iii.) presentation tasks, layouts and different modal and non-modal interactions and affordances as specified in the presentation data 1531, layouts and templates 1532, presentation state 1533; (iv.) interactive dialogue, question and answer sequences, question and answer strategies as specified in plans and questions 1537, user model 1534, goals 1536, evaluation 1535 and actions 1538; (v.) feedback loops, world and environment interactions for both physical and simulated worlds as specified in world and environment model 9800; (vi.) third party data and/or domain knowledge as specified in domain knowledge 1524 and third party data 1539; (vii.) statistical causes, cause-and-effect chains, causal effects and motivations, causal scenarios as specified in a suitable combination of any or all of the hypothetical and causal component 1510 and its sub-components 1511, 1512, 1513, 1514, 1515, 1516, 1517 and 1518; (viii.) human knowledge and supervision, or semi-supervision, such as in HKI 1518.

In an exemplary embodiment, interpretations may be personalized and/or transformed to cater to: (i.) different interpretation rules and procedures, interpretation briefs, interpretation processes and protocols as specified in interpretation rules and procedures 1542, interpretation brief 1547, and protocol context 1548; (ii.) scope and interpretation framing, pre-specified output formats and templates, and pre-specified protocols as specified in interpretation framing 1541, interpretation rules and procedures 1542, interpretation templates 1545, and protocol context 1548; (iii.) generally accepted interpreter domain knowledge and interactive context as specified in interactive context 1544, and interpreter domain knowledge 1546; (iv.) different scenarios, different interpretation viewpoints, conflict and dispute resolution, and inter-interpreter interaction and communication as specified in a suitable combination of any or all of the interpretation model component 1550 components 1551, 1552, 1553 and 1554.

FIG. 11 illustrates an exemplary embodiment in which the explanation 9141 and/or the selected interpretation(s) 9142 may be used in an actor model type of system, or a similar system, such as a reinforcement learning (RL) system, explainable reinforcement learning (XRL) system, robotic and autonomous machine systems, control engineering systems and other suitable embodiments. The evaluator 9400 is an optional component that receives the explanation 9141 and/or the selected interpretation(s) 9142 as input and adds evaluation information, for example, a flag indicating the priority of the incoming input, or a forecast of the potential impact. The evaluator 9400 may utilize different components in the explanation scaffolding 9101 and/or the interpretation scaffolding 9111. For example, the evaluation 1535 component may be utilized as an additional input to the evaluator 9400.

The planner 9500 may use the explanation or interpretation input either directly or after it has been processed via the evaluator 9400, and may use it to create or refine an action plan. The planner 9500 may utilize different components in the explanation scaffolding 9101 and/or the interpretation scaffolding 9111. For example, the goal 1536, plan and question 1537, and action 1538 components may be utilized as an additional input to the planner 9500. The planner 9500 may further utilize additional steps of approval, authority checking, planning optimization and other relevant actions in an exemplary embodiment.

The executor 9600 may receive input from the planner 9500 and may implement the sequence of actions and processes that make up the planned actions determined by the system by acting upon the environment 9700. The executor 9600 may give optional feedback back to the planner 9500. The executor 9600 may also receive feedback from the environment 9700 and modify its behavior accordingly.

The executor 9600 acts upon the environment 9700. The executor 9600 may utilize different components in the explanation scaffolding 9101 and/or the interpretation scaffolding 9111. For example, the world and environment model 9800 component may be utilized as an additional input to the executor 9600.

The exemplary embodiment in FIG. 11 illustrates one exemplary implementation and can be modified further with the addition and deletion of steps and components.

In one example, behavioral models (BM) and behavioral model hierarchies (BMH) may be incorporated as part of the input to the evaluator 9400 or the planner 9500. In another example, the evaluator 9400, planner 9500 and executor 9600 may be combined into a single component. In a further example, a Robotic Process Automation (RPA) system or an ERP system may also be used to implement part or all of the evaluator 9400, planner 9500 and executor 9600.

The executor 9600 may also be a human user that receives instructions from the automated system planner 9500 and that subsequently executes such instructions and reports back to the planner 9500 to interact with an automated system collaboratively.

The explanation scaffolding shown in FIG. 8 and the interpretation scaffolding shown in FIG. 9 may both be implemented and embodied using a suitable method for encoding and transmitting explainable rules for an artificial intelligence system, and/or a suitable method for encoding and transmitting a mixture of structured and unstructured data that is suitably marked up and/or labelled using a suitable markup or labelling mechanism. In an alternative embodiment, the explanation scaffolding and the interpretation scaffolding and part or all of the EIGS may also be embodied using a suitable hardware representation, which may be implemented either using flexible architectures like FPGAs, more static architectures like ASICs, analog/digital electronics, optical-electronic hardware, quantum computers or neuromorphic hardware. The transmission can be implemented entirely in hardware when using flexible architectures that can configure themselves dynamically. In an alternative exemplary embodiment, a named label may be assigned to any component or sub-component in an EIGS, which is then utilized to link such a named component symbolically. In said exemplary embodiment, a named label may be assigned to an XNN neuron, corresponding to a symbolic and human understandable representation of that particular feature or feature interaction represented by that XNN neuron. The named label may also be used to track model evolution within a model discovery process, such as one that may be implemented using an exemplary AutoXAI system. Named labels may also be used by the EIGS to summarize explanations and also to explore and represent invariances within the EIGS over time. Such invariances may help detect model robustness to Out of Distribution (OOD), anomalies and data shift events.

The semiotics component 1523 may implement a unique kernel labelling embodiment that allows the EIGS to label data into a progressive refinement of patterns, symbols and concepts from any data format that allows a pattern recognition kernel to be defined, together with a suitable key point description function and an activation maximization function.

An exemplary kernel labeler may be illustrated via an exemplary medical application embodiment utilizing a convolutional neural network (CNN) that is fully interchangeable with its explainable counterpart, a CNN-XNN system.

Figure 5:
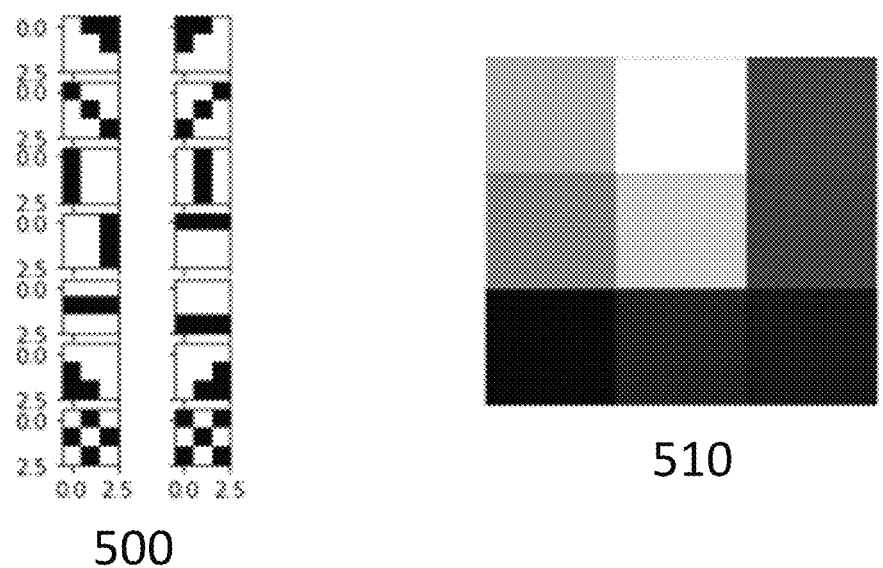
FIG. 5 is an exemplary embodiment of human defined kernel primitives.

A kernel primitive p 500 may be defined as a matrix of a certain shape being searched for in the respective filter being analyzed. FIG. 5 illustrates an exemplary human defined kernel primitive 500. The Kernel Labeler may initially analyze the first convolutional layer using human defined kernel primitives and may proceed to slide through the convolutional and pooling layers in the CNN architecture. A kernel primitive p may be defined as the same matrix size as the kernel size of the first convolutional layer. In an exemplary embodiment, the operation of a kernel is element wise multiplication, and the visual shapes of kernel primitives 500 may be based on human-defined knowledge, including shapes such as corners, diagonal lines and vertical lines found in a typical image.

Given a kernel primitive p, a set of human-defined kernel primitives $S_p$ may be defined.

Figure 6A:
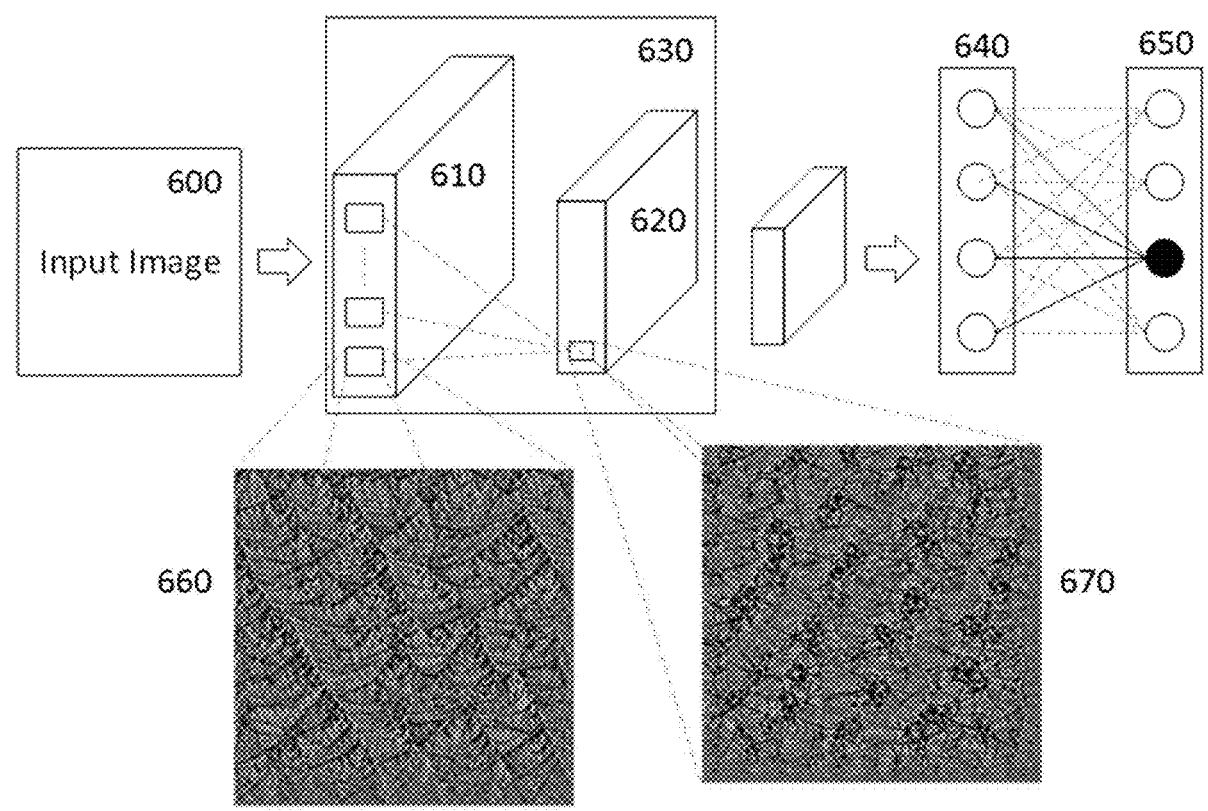
FIG. 6A is an illustration of an exemplary embodiment implementing sliding window primitives in a black-box CNN architecture.
Figure 6B:
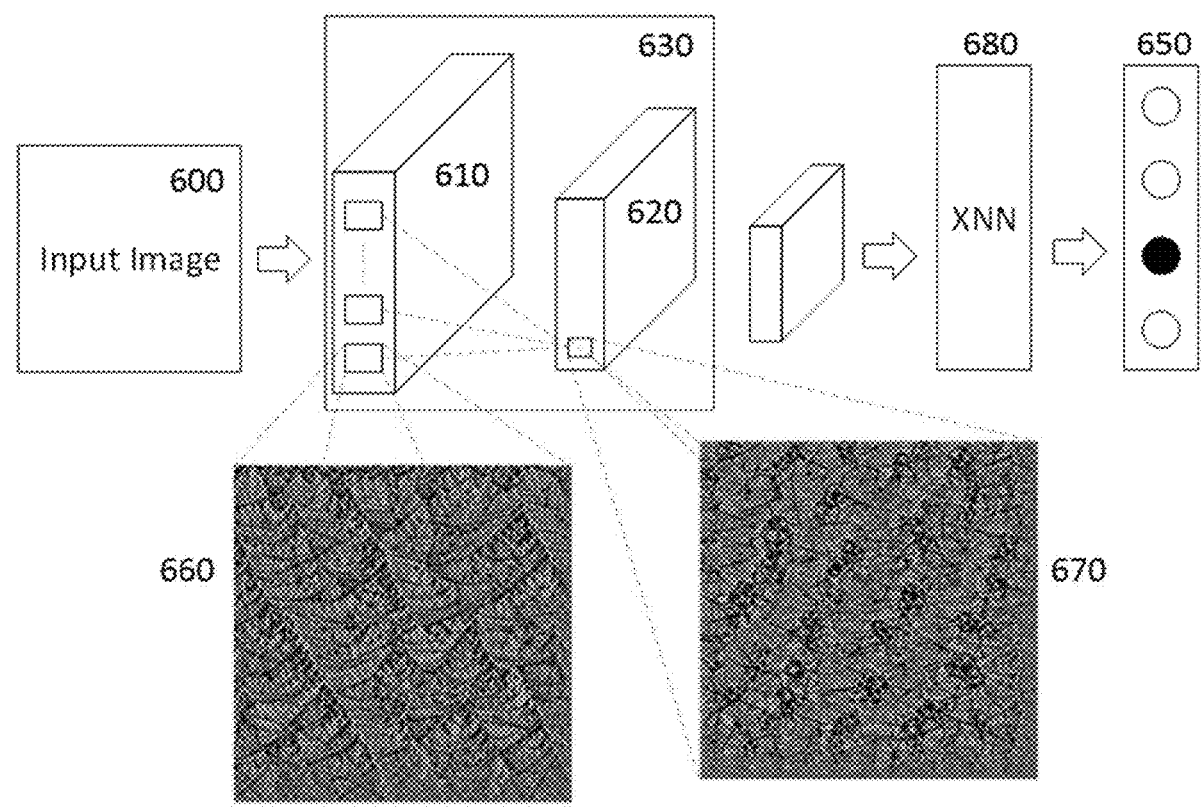
FIG. 6B is an illustration of an exemplary embodiment implementing sliding window primitives in a CNN-XNN architecture.

A set of human-defined kernel primitives $S_p$, where $S_p = [p_1, p_2, \ldots, p_n]$, may be defined for a particular CNN architecture, as shown in FIG. 6A, or CNNXNN architecture, as shown in FIG. 6B. A CNN architecture may include a fully connected layer 640 as a final step of the CNN architecture. A CNNXNN architecture may include an XNN component 680 as a final step of the CNNXNN architecture. The set of human-defined kernel primitives $S_p$ may represent the vocabulary to be used for the analysis of the first convolutional layer in a CNN or CNNXNN architecture. A descriptor d may be constructed for each kernel k in the first convolutional layer, having a length of the size of $S_p$. The descriptor d may contain a value for each human-defined kernel primitive 500 in the defined vocabulary, that is $S_p$, and this value may represent the presence of the kernel primitive in the kernel k. In the EIGS, the vocabulary $S_p$ may be defined in either component 1522, 1523, or 1524 and may be further labelled using metrics and dimensions component 1521.

The presence of a kernel primitive p in a kernel k may be measured by analyzing the weights of k 510 to locate the shape of p within kernel k. The shape may be detected if the value difference of each combination of weights of the shape in kernel k would not exceed a threshold a and if the threshold a of the kernel primitive is not exceeded for N E R occurrences. The detection of primitives may be scale, rotation, and spatially invariant. This enables the detection of shapes that are on different scales, at different rotations and at different positions.

The descriptive analysis of the first convolutional layer may be the initial step of the Kernel Labeler. FIG. 6A illustrates the analysis of the remaining layers, using the sliding window primitives method, of a black-box CNN architecture. FIG. 6B illustrates the analysis of the remaining layers, using the sliding window primitives method, of a CNN-XNN architecture.

The initial layers in an exemplary machine learning model may be constructed of filters which look for basic patterns such as horizontal and vertical lines. However, deeper layers may include filters that look for complex patterns as primitives and the previously discussed algorithm to detect the presence of primitives may not yield the optimal results, necessitating the need to utilize a suitable component integration technique, such as activation maximization (AM) or multifaceted feature visualization (MFV), to project patterns onto the input space.

The component integration technique may generate a synthetic image for each filter in the layer. The component integrated filters 660, 670 of the primitive layer 610 and the current layer 620 may be analyzed using key point description techniques that aim to extract distinctive invariant features 400 from images, in this example. The EIGS Kernel Labeler may implement key point descriptors using a combination of the SIFT, SURF, GLOH or any other contemplated method.

The next step performed by the EIGS Kernel Labeler may cluster similar features to create a vocabulary of distinctive features. Distinctive features and their respective kernels may be represented using a variety of methods including, but not limited to, histograms, eigenvectors, multi-dimensional descriptors, spatial bag of word models, scale invariant models, rotation invariant models, convolutional patterns, cross-correlation patterns, auto-correlation patterns, Hugh transforms, Radon transforms, Fourier transforms, integer/real/complex/quaternion/octonion transforms, Walsh functions, state-space transforms, phase-space transforms, Haar and non-Haar wavelets, generalized L2 functions, fractal-based transforms, Hadamard transforms, categorical descriptors, multi-dimensional Bezier curves, subsets of an explainable neural network, and suitable alternative representations. As illustrated in FIG. 4, the bag of visual words (BoVW) technique (Yang et al., 2007; Yang et al., 2010, Xu et al., 2009), may be used to create a codebook 420 of features, such that similar distinctive features are grouped together 420. BoVW may be used to cluster the N-dimensional features 410 using a suitable clustering algorithm such as K-Means, obtaining a set of centroids, where each centroid represents a group of similar features. Key points detected in synthetic images of the primitives and the layer filters being analyzed may be associated with the nearest centroid 430 by the clustering algorithm. A descriptor 440 may be constructed, for each primitive and filter, representing the frequency count of each centroid. Similarity metrics, such as cosine similarity, may be used by the Kernel Labeler to identify the progression of features from basic shapes to complex patterns in a CNN architecture or other similar progressively structured machine learning architecture. Translational invariance and translation equivariance methods may also be used by the Kernel Labeler to ensure that translation variances from basic shapes to more complex patterns are handled correctly. The use of the novel Kernel Labeler mechanism enables explainable machine learning models to achieve and practically implement neurosymbolic processing, allowing connectionist models such as CNN-XNNs to be seamlessly linked into larger AI and ML systems that involve logic and symbolic processes and vice-versa.

The Kernel Labeler component integration method implementation performance can be improved with the addition of regularization techniques, such as Jitter (Reed et al., 1992), total variation (TV) (Mahendran et al., 2016) and center-biased (Nguyen et al., 2016) techniques to generate results that are more interpretable to human users.

In an exemplary medical application, a chest X-Ray is analyzed for possible pneumonia. The exemplary medical application may require the output 650 to be derived using an interpretation template method such as the Kernel Labeler method. The EIGS Kernel Labeler may analyze the progression of patterns using the sliding window Kernel Labelling technique 630 for the respective classification label from a set specified in the taxonomy 1522, and that may need to be output according to the interpretation template 1545. The EIGS Kernel Labeler may visualize and analyze the feature maps produced by the convolutional layers and calculate the component integration value for the respective filter. The component integration may then be aggregated to determine the activation of a specific filter or set of filters for the input image 600, and thus associate the correct label for the detected pattern, symbol or concept within the input image 600.

An exemplary Kernel Labelling embodiment may be combined with the CNN-XNN Backmap to project the output classification results, through the XNN component 720 and the CNN component 710, back to the input space. For the medical application example, the image pixels that are deemed to be the most important for the classification output can then be highlighted appropriately by the EIGS, as illustrated in FIG. 7. As illustrated in FIG. 3, Backmap integration would enable the EIGS to project relevant elements of the output explanation and/or interpretation back to the input space, making it easier for system users to understand and comprehend the resulting explanation and/or interpretation.

The EIGS Kernel Labeler can be used on any data format that allows for a pattern recognition kernel, key point description function, and component integration function to be defined on that data format. For example, the EIGS kernel labeler invention can be used on 3D scans using 3D primitives, 3D key point description function and a 3D Activation Maximization function. For a further example, the EIGS kernel labeler invention can be used on speech data using a phoneme based audio primitive, spectrogram based key point description function working in Fourier transformed space, and an activation maximization function based on audio data. The kernel labelling embodiment can thus be extended to video, sound, speech, text, 3D scans, tabular data, haptic data, and other suitable data formats that can be processed by component 1523 in the EIGS.

(Hoffman et al., 2018) treat explanations as an interaction with the system user and propose an XAI system explanation process framework. In this exemplary evaluation model, a user initially receives some form of instruction, task or new goal, that is eventually followed by an XAI system generated explanation. The quality evaluation of an explanation may depend on the quality and the satisfactory level of an explanation. The explanation quality may update the user's mental model, thus increasing (or appropriately decreasing) trust in the XAI system. As more trust is built up, the user can use the XAI system more appropriately to achieve better performance in meeting the user goals and tasks.

The explanation scaffolding 9101 and the interpretation scaffolding 9111 is compatible with the explanation process framework proposed by (Hoffman et al., 2018). The EIGS may use the various user characteristics in the user model 1534 to ensure the quality of the contextualized judgement.

(Hoffman et al., 2018) treat the quality of an explanation an a priori decontextualized combination of factors such as precision and clarity and offers a list of questions that may be used in an evaluation process.

The EIGS may personalize and/or transform explanations and interpretations using a combination of components 1523, 1524, 1542, 1547, and 1548 to learn the appropriate response to the explanation triggers and ensure quality and satisfiability of explanations.

An exemplary embodiment may treat the satisfactory level of an explanation as a posteriori contextualized judgement that is defined as the level of understanding of the user for an explanation generated for a particular need of an explanation (i.e. an explanation trigger). Attributes of satisfaction may include usefulness, trustworthiness, and completeness of the explanation.

The EIGS may personalize and/or transform explanations and interpretations into presentation tasks, layouts and different modal and non-modal interactions and affordances as specified in a combination of components 1531, 1532, 1533, 1536, 1537, 1538, 9800, and 1544 to cater to multiple types of explanation triggers, and ensure the satisfiability of the system user in a posteriori contextualized judgement and hence optimize the satisfactory level of the explanations and interpretations.

The EIGS may personalize and/or transform explanations and interpretations to incorporate and meet various goals, plans, milestones, evaluation criteria and constraints specified in a combination of components 1535, 1536, 1537, 1538, 9800, and 1544 to ensure quality in a decontextualized judgement and satisfiability in a contextualized judgement.

The DARPA XAI explainable notional model (Gunning, 2016) uses different axes for explainability, prediction accuracy, explanation effectiveness and learning performance. Explainability in DARPA's model is accurately modeled by a notion of model interpretability and output interpretability. An exemplary embodiment may adopt the same definitions for prediction accuracy, learning performance and explanation effectiveness as the DARPA model.

The DARPA model also mentions the concept of the complexity of an explanation and the usefulness of an explanation. Similarly, (Doshi-Velez et al., 2017) relate the time taken by a system user to understand an explanation as a proxy for its complexity and describe a measure and localization of incompleteness of an explanation as an evaluation feature which may be adopted in evaluation component 1535.

In this embodiment, the complexity of an explanation is related to its degree of output interpretability, the intended system user expertise level of the explanation, the intrinsic domain specific complexity of the subject matter being explained, and the overall length and compressibility of the explanation.

The usefulness of an explanation may be related to its degree of global or local interpretability and output interpretability, which in turn are related to the definition of white-box, grey-box and black-box. An explanation may be useful if output by a white-box explainable system, partially useful if output by a grey-box explainable system, and mostly useless if output by a black-box explainable system.

An exemplary embodiment may provide a domain-specific way of optimizing explanations using a taxonomy of approaches that evaluate interpretability. An exemplary embodiment may implement the three evaluation approaches defined in (Doshi-Velez et al., 2017), namely: application-grounded, human-grounded, and functionally-grounded.

Application-grounded embodiments may evaluate interpretability by having humans emulate the functionality of the entire application and its respective tasks, and subsequently comparing the output of the interpretable AI system against the human standard.

Human-grounded embodiments may evaluate interpretability by conducting simpler human experiments that represent the core of the application, which may be further divided into three categories: (i.) binary choice, where humans are given multiple pairs of explanations from which they choose the highest quality explanation; (ii.) forward prediction, where humans are given an input and an explanation and select the corresponding output; (iii.) counterfactual simulation, where humans are given the input, output and an explanation, and should mark the changes required for the application to correctly predict the output.

Functionally-grounded embodiments may evaluate interpretability by utilizing a formally defined interpretation metric to measure the quality of the explanation, in a similar manner to most of the DARPA XAI evaluation metrics.

Using a human-grounded approach, input and output pairs $\langle I, O \rangle$ may be presented to human judges who produce an explanation $E_h$ for each input-output pair. The same input and output pairs may be presented to the relevant XAI model being evaluated, which may produce an explanation $E_s$ for each input-output pair. Some suitable distance or scoring function $S_h$ may compare $E_h$ with $E_s$, giving an evaluation function $V_h$ of the form: $V_h(\langle I, O, E_s \rangle, \langle I, O, E_h \rangle) = S_h(E_s, E_h)$.

Using a functionally-grounded approach, human judges may be presented with an input, output, explanation tuple $\langle I, O, E_s \rangle$ and then may be asked to provide a subjective score $S_h'$ that in their opinion best represents the quality or suitability of Es given the domain and query context and any other information that the human judges deem suitable for the evaluation task. A suitable machine learning method may be used to learn a domain specific function Vs which is trained on $\langle I, O, E_s \rangle$, $S_h'$ pairs.

An exemplary embodiment may implement a learnt function Vs to perform additional domain-specific optimization of induced XAI models and logically equivalent grey-box and white-box explainable machine learning systems by creating an optimized domain-specific function Vo from Vs as follows:

$$V_o(\{\langle I_1, O_1, E_{s1} \rangle, \ldots, \langle I_n, O_n, E_{sn} \rangle\}) = \underset{i \in n}{\mathrm{argmax}}\, V_s(\langle I_i, O_i, E_{si} \rangle)$$

Vo can be used to optimize XAI systems in various ways, including but not limited to, (i.) the selection and ranking of explanations from a range of possible explanations; (ii.) modification of an explanation to make it more amenable for human use; and (iii.) transformation of an explanation to make it more useful in a domain-specific context. Vo can be learnt and optimized further using methods such as back-propagation, Viterbi, and other suitable methods.

In an exemplary embodiment, in a sport, nutrition and personal health application context, the EIGS may use a combination of: (i.) personal health monitoring hardware, such as a wearable electronic watch or bracelet with embedded motion sensor, pace counter and heart rate sensor; (ii.) tabular data log containing dietary entries supplied by users, some of which are incomplete and sporadically erroneous and contain English language entries for various food and drink items consumed by the users; (iii.) data from a wireless data enabled smart personal weight scale, which has missing data gaps. Three explainable models 904 may be utilized to process the three sources of information: (i.) an XNN may process the personal health monitoring data, (ii.) an XTT may process the tabular data, and (iii.) a PR-XNN may process the time series data. The model fusion and links component 9064 may be used to fuse the outputs from the three models together, with the aid of the metrics and dimensions component 1521 that ensures that all units of data from different hardware sensors in (i.) are correctly converted to the same base units. The taxonomies and ontologies component 1522 may add appropriate taxonomy and ontology information the model data, such as through the use of the ISO/TS 18308 Electronic Health Record and ISO/HL7 27931 Health Data Exchange standards.

An exemplary EIGS may implement a Causal DAG in hypotheses and concepts component 1511, as illustrated in FIG. 12, based on an example adopted from (Gaskin, 2016).

The causal DAG may explore the concept of whether exercise 1420 moderates the relationship between diet 1410 (the independent variable) and weight loss 1440 (the dependent variable). The causal DAG may be processed by the interactions and moderators component 1513, that creates an automatically named variable 1430, "diet×exercise", to represent the moderation.

The EIGS may also use a controls and quality component 1512 to spot data quality issues in the personal health data and the tabular data log and correct them when possible.

The EIGS may use the associations and assumptions component 1515 to utilize the XTT text-matching capabilities to assign a correct nutritional class for the food and drink item, utilizing a taxonomy supplied by taxonomy component 1522. After this nutritional class assignment, the EIGS may use the partitioning information from the XNN model 904 in combination with the nutritional class assignment per user to classify the diet 1410 data into low intensity levels of dieting ("Low Diet") or high intensity levels of dieting ("High Diet"), grouped per user. The EIGS then may use the interaction and moderator component 1513 to estimate the values for the moderator variable Diet×Exercise 1430.

The EIGS may further implement the domain knowledge component 1524 to determine the effectiveness of dieting on exercising that will be used in subsequent generation of English language summaries by the EIGS.

The results may be packaged in the explanation scaffolding 9101 and sent to a filter 911 using the EFI model as illustrated in FIG. 10.

The interpretation template 1545 may be used to indicate that the EIGS should output results for weight loss, the classification of diet intensity levels, the moderator analysis, and two English text interpretations of the results, one at an expert system user level, and one at Level 2 low intermediate English language level system user level.

The interpretation rules and procedures component 1542 may be used to instruct the EIGS on how missing weight data from an exemplary model is interpolated and filled in automatically. It is further contemplated that interpretation rules may include a combination of appropriate logic connectives, for example, for Boolean logic, a combination of AND, OR, XOR, NOT, IFF/XNOR, NAND, NOR, IF . . . THEN/IMPLY, CONVERSE/NIMPLY, and so on.

The interpretation brief 1547 may combine the explanation 9141 that has been created so far from the three combined models together with the interpretation template 1545 to create an interpretation 9142. This interpretation 9142 may be visualized using the presentation data 1531 and layouts and templates 1532, with any relevant state information stored in presentation state 1533.

FIG. 12 shows four exemplary interaction visualization diagrams 1400 that may be produced by an exemplary EIGS system, showing different outcomes. The English text interpretations produced by the EIGS present the explanatory information to the system user at different expertise levels, for example, the explanation "Exercise positively moderates (amplifies) the relationship between diet and weight loss", which is aimed at an expert system user, is output for a low intermediate English language level system user level as "Exercising makes dieting more effective".

In another exemplary embodiment, in a medical application context, an EIGS system controls a 3D computed tomography (CT) scanning machine, and a positron emission tomography (PET) scanning machine to get an enhanced explanation of a medical diagnosis in a reliable and practical manner, with additional inputs from different patient health records and data from sources like tabular data representing biopsy results. The EIGS system may control a robotic needle biopsy system that accurately performs biopsies with minimal invasion for patients.

An exemplary EIGS system can be implemented using a combination of CNN-XNNs, XNNs and induced XAI models, with HKI support to encode domain-specific knowledge from medical experts in some suitable supervised, semi-supervised or unsupervised manner. The robotic needle biopsy system control can be implemented using an XRL agent with a behavioral model for assured safe operation, with real-time input from a PR-CNN-XNN that analyses CT scan data to monitor and guide the needle accurately through the optimal path that ensures minimal invasiveness and damage to the patient while constantly predicting the needle path to ensure that potential damage to the patient is minimized or eliminated pre-emptively.

For example, assume that an EIGS system scans patients to determine the presence or absence of lung cancer. In this example, the HPTC taxonomy is used as specified in taxonomy component 1522. The EIGS system may assign the CT scan data coming from the CNN-XNN model 904 the National Provider Identifier (NPI) code "2471C3401X". The PET scan data coming from another 3D CNN-XNN model 904, may use the CPT taxonomy and is tagged with CPT code "A9597", designating the use of PET for a diagnostic tumor identification procedure.

The exemplary EIGS-based machine learning system automatically knows that such data should be grouped together with similar radiology data (which is assigned a parent code of "261QR0200X") and has originated from a radiation therapy center with Medicare specialty code "74". Furthermore, via the Medicare specialty code that is common to both models, in this example, code "30", signifying a medical provider type of physician/diagnostic radiology, the EIGS system knows that the resulting explanation 9141 and/or interpretation 9142 needs to have a level III area of specialization type of explanation, together with an explanation aimed at a level of a typical educated patient.

An exemplary EIGS system uses the taxonomy information to locate the appropriate medical diagnostic protocol loaded in domain knowledge 1524, interpretation rules and procedures 1542, and protocol context 1548 components. In this example, the EIGS system may determine that the appropriate regulatory authority is the FDA, and then uses data in the Guideline Interchange Format (GLIF) to load the applicable FDA approved medical diagnostic guideline protocol needed for this particular case (as represented by the input query 902). In this example, the EIGS system is effectively acting as a guideline execution engine.

In this example, the application uses a causal model in hypotheses and concept component 1511 together with information in the model fusion and links component 9064 and the metrics and dimensions component 1521 to fuse the CT data with PET scan data via an CNN-XNN backmap as illustrated in FIG. 7. The explainer 908, using the explanation scaffolding 9101, has determined that the CT and PET scan data together with other relevant explanatory information from the model 904 determines that there is a medium probability of lung cancer cells and assigns a diagnostic code of "D47.09" and a recommendation for a follow-up biopsy procedure. The counterfactuals component 1517 in the explanation scaffolding 9101 is then used to calculate the probability of adverse effects of the probable lung cancer if the follow-up biopsy procedure is performed against the probability of adverse effects if the biopsy is not performed, which for this example, gives a favorable result recommending a biopsy procedure.

The EIGS system may output an explanation 9141 containing the fused image data from the CT and PET scan, together with diagnostic text output, as illustrated in FIG. 3. An exemplary EIGS also outputs a recommendation for a biopsy in its interpretation 9142, which is presented as part of the output in FIG. 3. Hidden from the output, but present in the explanation scaffolding goals-plans-actions components 1536, 1537, and 1538, is information to be used by the robotic needle biopsy system to execute the recommended procedure, after the appropriate authorization has been given by the system user and the appropriate consent has been received from the patient, in accordance with the interactive context 1544 and protocol context 1548.

In an exemplary embodiment, an EIGS system may implement an Identify-Assess-Resolve (IAR) framework to identify risks, scenarios, objectives and goals, while subsequently assessing impacts, costs and consequences, and finally recommend ranked resolution actions and plans. It is further contemplated that the IAR framework be implemented in conjunction with an XRL agent to take advantage of the explainable action-policy.

In a further exemplary embodiment, an EIGS system may implement a recommendations system that can match items to users, users to items, items to items, and users to users, while segmenting and explaining user behavior and predicting what recommendations will incentivize users to increasingly perform more desirable actions while increasingly refraining from taking undesirable actions. It is further contemplated that a variety of data points and signals, such as time, lifecycle models, and a cost-benefit model may be used to refine the recommendations.

In another exemplary embodiment, an EIGS system may implement a multiple choice or scenario selection and testing system, such as A/B testing, multi-variate testing, or a causal n-choice system.

In another exemplary embodiment, in a predictive maintenance context, an EIGS system is implemented using embedded mobile hardware in an edge-based system running on an autonomous vehicle, such as an autonomous car or truck. The EIGS system receives input from a PR-XNN based Model 904 that analyses audio samples recorded from various mechanical points around the autonomous vehicle, to determine whether there is an impeding mechanical fault together with an estimate of the severity of such fault.

An appropriate statistical model in associations and assumptions component 1515 determines whether the autonomous vehicle should be booked in for a scheduled maintenance service, or in case of an impeding failure, an emergency maintenance service. In this example, a scheduled maintenance service of the vehicle rear electric motors is determined to be appropriate. This determination is output within the explanation 9141, which is then sent to the main EIGS system controlling the autonomous vehicle. The main EIGS system may be connected to the vehicle user's smartphone, and may use tabular information representing the vehicle user's meeting and travel schedule to find appropriate timeslots for the recommended service. The main EIGS system component 1530, which is implemented as part of the autonomous vehicle dashboard display, may be used to display a brief explanation of why a service is needed, an estimate of such service cost, recommended timeslots and asks the vehicle user for the appropriate authorization. After authorization, the main EIGS system may then subsequently transmit the explanation 9141 to the service depot, confirms a timeslot for such service, and then may use the goals-plans-actions components 1536, 1537, and 1538 to determine the optimal times when it can drive itself back and forth to the service appointment while minimizing the inconvenience to the vehicle user.

In an exemplary embodiment, an EIGS system may use an Explanation Structural Model (ESM) to implement Explanation Scaffolding 9101, and Candidate Explanations 9102.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A system for providing explanations and interpretations, the system comprising a processor and a memory on which is stored computer program code instructions, wherein the processor operates to provide:
    an explainable model configured to receive an input query and return a model output, wherein the model output comprises an answer and a model explanation;
    an explanation component configured to receive the model output to produce an explanation using an explanation scaffolding, the explanation scaffolding comprising a plurality of components including:
        an explanation model component, comprising the model output indicating the answer, the model explanation, and a model fusion and links component, wherein the model fusion and links component is configured to store metadata and information associated with one or more links between one or more systems and databases;
        a hypothetical and causal component, configured to model at least one cause-and-effect relationship by forming one or more structural equation models, structural causal models, and/or causal directed acyclic graphs; and
        a scenario, interaction, and presentation component; and
    a plurality of interpreters comprising a plurality of interpretation components, the plurality of interpretation components forming an interpretation scaffolding and configured to receive the answer, the model explanation, and the explanation scaffolding to produce an interpretation, the interpretation scaffolding comprising a plurality of interpreter beliefs components, wherein the interpretation scaffolding isolates each of the interpreter beliefs components from each of the other interpreter beliefs components;
    wherein receiving, on the explanation component, the model output using the explanation scaffolding comprises:
        receiving, on the explanation component, an explanation scaffolding data structure, the explanation scaffolding data structure comprising each of the plurality of components and defined linkages between the plurality of components; and
        deconstructing the explanation scaffolding data structure into an explanation.

2. The system of claim 1, wherein the hypothetical and causal component further comprises an abductive logic system for diagnosing an observed effect to identify a cause of the observed effect and one or more recommendations, the recommendations comprising a course of action to remedy the observed effect.

3. The system of claim 1, wherein the hypothetical and causal component further comprises one or more hypothesis evaluation components and a plurality of concepts associated with groupings of one or more hypotheses,
wherein each grouping of one or more hypotheses connects one or more concepts in the plurality of concepts by identifying one or more expected relationships between propositions for the one or more concepts, and
wherein a conceptual framework is formed from the one or more expected relationships, and
wherein the hypothetical and causal component is further configured to cluster different types of explanations into concepts using a cognitive chunk model, implement a confirmatory factor analysis, and/or implement an explanatory factor analysis.

4. The system of claim 1, wherein the interpretation scaffolding comprises:
an explanation and interpretation scenario component;
a framing, protocol, and contextual component; and
an interpretation model component.

5. The system of claim 1, wherein the hypothetical and causal component further comprises:
a hypotheses and concepts component configured to store information corresponding to one or more hypotheses applicable to the explanation, wherein the one or more hypotheses include one or more of:
 a trial hypothesis comprising a suggested outcome based on evidence, wherein the hypotheses and concepts component is configured to test the evidence to confirm or reject the trial hypothesis;
 an abductive hypothesis comprising a suggested explanation regarding a goal to be achieved;
 a statistical hypothesis; or
 a causal hypothesis identifying whether one or more of a plurality of features recognized by the explainable model is an effect of a cause triggered by an interaction of one or more of the plurality of features;
a controls and quality component configured to:
 generate an output within one or more predetermined parameters;
 identify and apply one or more predetermined compliance constraints with tolerance parameters;
 store and retrieve information indicating a state of qualitative or quantitative information of a plurality of variables and data within the system, and determine whether the variables and data within the system are internally consistent;
 apply one or more of standardization, cleansing, data transforms, data profiling, data matching, data linking, data conformity checks, data accuracy checks, data precision checks, data bias checks, and data interpolation methods to the variables and data within the system;
 apply one or more data privacy and access rules to the variables and data within the system;
 trigger one or more actions or modify and configure one or more constraints and activating events and triggers in a behavioral model;
 validate, compare, and analyze the variables and data within the system in relation to a set of validated reference data to identify one or more new or discrepant values; and
 apply one or more of data transforms, timestamp checks, data freshness checks, and data retention policy compliance of the variables and data within the system against a defined service level agreement,
an interactions and moderators component;
a mediations component;
an associations and assumptions component;
an interventions component; and
a counterfactuals component.

6. The system of claim 5, wherein the interactions and moderators component is configured to discover a plurality of moderators, the moderators comprising categorical or quantitative variable that affects a relationship between one or more interactions,
wherein the interactions and moderators component is configured to discover the plurality of moderators by at least one of a correlation analysis method and a variance analysis method; and
wherein the interactions and moderators component further comprises a latent variable model.

7. The system of claim 5, wherein the system includes the mediations component, and wherein the mediations component comprises statistical and causal mediations applicable to the explainable model and wherein the mediations component is configured to identify one or more mediator variables indicating a relationship between one or more independent variables and one or more dependent variables.

8. The system of claim 7, wherein the mediations component is further configured to:
identify moderators from the interaction and moderator component affecting the relationship between one or more independent variables and one or more dependent variables;
create a new mediated moderation path associated with a new mediator value by applying a moderator effect via the new mediator value and a new indirect path from the independent variables to the dependent variables; and
assign a label for the moderator effect and the independent variables and the dependent variables according to the identified moderators.

9. The system of claim 5, wherein the associations and assumptions component is configured to determine one or more of:
statistical associations between sets of data variables;
conditional probabilities between data variables;
inferences and associations obtained from data using conditional expectation methods;
answers to conditional probability sentences of the form $P(y|x)=p$, where the probability of an event $Y=y$, given that $X=x$ was observed, is equal to p; and
a scenario analysis.

10. The system of claim 5, wherein the interventions component is configured to identify a plurality of potential interventions, and is configured to use the potential interventions to determine one or more of:
conditional probabilities that distinguish between causal relationships from correlative relationships stored in the associations and assumptions component;

one or more of: causal adjustments; multiple interventions; back-door identification and estimation methods; front-door identification and estimation methods; conditional interventions;
covariate-specific effect identification and estimation methods; inverse probability weighting and estimation methods; confounder identification; and suppressor variable identification;
causal inference obtained from using causal interventions; answers to conditional probability sentences; and
a scenario analysis.

11. The system of claim 5, wherein the controls and quality component is further configured to integrate with a semiotics component and a domain knowledge component by performing one or more checks, comprising:
checks against a predetermined range of values or static interrelationships;
checks against aggregated processes and functions held in domain knowledge of the domain knowledge component;
outlier checks and exception case flagging;
drift checks against one or more nominal conditions that are prespecified or automatically discovered by a machine learning system;
checks against one or more predefined business as usual expectations;
checks using an explainable autoencoder/decoder system for drift, shift and abnormality detection,
wherein the checks are performed using one or more of: simple generic aggregation rules, complex logic functions on a group of attributes of data input to the processes and functions held in the domain knowledge, and automatically discovered checks discovered via a machine learning process ran against the well-known processes and functions held in the domain knowledge.

12. The system of claim 5, wherein the interactions and moderators component is configured to:
identify statistical correlations and causal interactions in the explainable model, and store the statistical correlations and causal interactions as one or more of:
transformations and mappings of subsets of data features;
predictions from information embedded in a reconstructed state space, a latent space, and/or a phase space;
co-occurrence statistics indicative of cause-and-effect; and
estimator functions and estimands together with a set of corresponding resulting estimates, wherein the system is configured to determine an estimate from an estimand using the estimator functions, and wherein the estimator functions comprise one or more of a point estimator or an interval estimator.

13. The system of claim 5, wherein the counterfactuals component is integrated with a continuous or discrete dynamic systems model, phase space model, recurrent feedback control system model and is configured to identify one or more:
one or more of: hypothetical adjustments; hypothetical interventions; deterministic and non-deterministic counterfactual determination methods; abduction estimation methods; action estimation methods; prediction estimation methods; consequence estimation methods; attribution of causation estimation methods; and direct and indirect effect estimation methods;
causal inference obtained from using causal counterfactuals;
answers to conditional probability sentences of the form P(yx|x', y')=p, provided that the probability of an event Y=y, had X been x, given that X was observed to be x' and Y to be y', is equal to p; or
answers to a scenario analysis.

14. The system of claim 4, wherein the framing, protocol, and contextual component comprises an interpretation framing component, an interpretation rules and procedures component, a protocol context component, an interpretation brief component, an interpretation templates component, an interpreter domain knowledge component, an interpreter beliefs component in the plurality of interpreter beliefs components, and an interactive context component,
wherein the interpretation framing component is configured to identify a framing of the interpretation using one or more models, representations, and/or simplifications to be applied by the interpretation component,
the interpretation rules and procedures component is configured to apply one or more interpretation rules and procedures;
the protocol context component comprises a protocol to be used when processing the explanation scaffolding; and
the interactive context component comprises one or more interactive and iterative processes to be tracked by the interpretation component.

15. The system of claim 14, wherein the interpreter domain knowledge comprises domain specific knowledge available to a plurality of interpreters, and wherein each interpreter beliefs component in the plurality of interpreter beliefs components comprises a combination of domain-specific and domain-independent knowledge and scenario-specific information.

16. The system of claim 14, wherein the interpretation model component comprises a scenario model, interpretation model, selection model, and conflict resolver component;
wherein the scenario model comprises information specific to a scenario observed by the interpretation component;
wherein the selection model identifies a selection process and method for ranking or scoring the interpretations resulting from the interpretation component; and
wherein the conflict resolver component is configured to identify one or more conflicts relating to the interpretation component and action triggers configured to be activated when one or more of the conflicts cannot be resolved.

17. The system of claim 1, further comprising a semiotics, taxonomical, and ontological component comprising a metrics and dimensions component, a taxonomies and ontologies component, a semiotics component, and a domain knowledge component, wherein:
the metrics and dimensions component comprises information regarding different systems of measurement and one or more of:
underlying units and dimensions of measurement comprising one or more of: a distance function; a differentiable manifold function; a translation, scale and rotational invariant metric function; a vector space metric; a multiset function; and a topological function;
a relationship between the underlying units and dimensions;
a relationship with a base standard topological space comprising at least one map, atlas, or transition map;

a conversion relationship to a base standard metric system; and
a translation process from a machine readable format to a human readable format or from a human readable format to a machine readable format.

18. The system of claim 17, wherein the semiotics, taxonomical, and ontological component is further configured to:
transform encoded information and units used by machine learning systems;
implement a gradient descent function and/or a dynamic programming function to output a result in a format specified by a subsequent machine learning system;
link taxonomies and ontologies to causal models stored in the hypotheses and concepts component; or
combine knowledge found in taxonomies and ontologies with human-generated knowledge and machine-generated knowledge.

19. The system of claim 17, wherein the semiotics, taxonomical, and ontological component further comprises a third-party data component configured to read and write a set of domain-specific knowledge to the semiotics, taxonomical, and ontological component and a semiotics component configured to implement one or more sign identification methods (kernels) and kernel labelling methods for one or more different transmission modalities of a plurality of symbols;
wherein the semiotics component comprises:
a plurality of syntactical models one or more properties and interrelations of the symbols based on a representation of the symbols; and
a plurality of semantical models comprising one or more links with taxonomies and ontologies indicating one or more properties of the symbols.

20. The system of claim 1, wherein the explainable model and/or explanation component are implemented as a hardware circuit, wherein the hardware circuit comprises one or more of an application specific integrated circuit (ASIC), analog circuit, digital circuit, optical-electrical circuit, field-programmable gate array (FPGA), computer processing unit, graphics processing unit, Neuromorphic computing hardware, and Quantum computing hardware.

21. The system of claim 1, wherein the scenarios, interactions, and presentation component comprises:
a presentation data component comprising data used to present the explanation;
a layouts and templates component comprising layout and format information,
a presentation state component comprising information identifying a state and history of a presentation layer;
a user model, wherein the user model provides a partial or full model of a plurality of users of the system and identifies whether users are human or automated, and is configured to associate a user profile to one or more users of the system, and wherein the scenarios, interactions, and presentation component is configured to constantly update the user model based on new information regarding the users;
an evaluation component configured to evaluate and log one or more of: a quality, accuracy, precision, complexity, usefulness, satisfaction, fairness, bias, authority, precedence, and effectiveness of the explanation;
a goals component comprising one or more system user goals, a plans and questions component configured to represent and execute one or more plans oriented by the system user goals, and an actions component comprising an action selection policy and a set of allowed actions, wherein the actions component is configured to identify and select a next action for the explainable model to perform and/or output; and
a world and environment model comprising a plurality of models of an interaction environment with which the explainable model is configured to interact and a plurality of models of an external environment beyond the explainable model, wherein one or more of the models of the interaction environment and models of the external environment comprise a behavioral model, a behavioral model hierarchy, an action trigger, and a feedback loop.

22. The system of claim 1, wherein a filter is configured to selectively apply a specified amount of noise to the input query and/or the model output according to a predetermined noise factor.

23. The system of claim 1, wherein the explainable model utilizes secure multi-party computation; and
wherein the system further comprises an access control component, wherein the explanation scaffolding is stored within the memory as the plurality of components, and wherein the access control component is configured to authenticate a plurality of parties and selectively control access to the plurality of components by the plurality of parties, comprising enabling access to at least one component in the plurality of components by a first party in the plurality of parties and enabling access to at least one other component in the plurality of components but not to the at least one component in the plurality of components by a second party in the plurality of parties.

24. The system of claim 1, wherein the explainable model comprises a plurality of combined decentralized explainable models, wherein each of the plurality of explainable models comprises local samples unique to each explainable model.

25. The system of claim 1, wherein the explanation comprises one or more user-centric explanations of one or more of the following types:
how-type explanations, why-type explanations, why-not-type explanations, what-if explanations, how-to, but-for, counterfactual explanations, and what-else explanations.

26. The system of claim 1, wherein the model output further comprises a justification corresponding to the answer and/or model explanation.

27. The system of claim 1, wherein at least one of the plurality of interpreters is configured to receive the explanation scaffolding by a process comprising filtering, with a filter component, deconstructed explanation scaffolding data, selectively removing data from the deconstructed explanation scaffolding data based on a user profile, and outputting filtered explanation scaffolding data to at least one of the interpretation components; and
wherein the filter component comprises an additional explainable model, or wherein the filter component is configured to apply a learnt function for performing a domain-specific optimization of the explainable model.

28. The system of claim 1, wherein the explanations comprise one or more of: local explanations, global explanations, post-hoc explanations, ante-hoc explanations, group explanations, user specific explanations, and summary explanations.

29. The system of claim 1, further comprising an identity-assess-resolve framework configured to identify one or more risks, scenarios, objectives, and/or goals, and assess a plurality of impacts, costs, and/or consequences of the identified risks, scenarios, objectives or goals, and recommend a ranked resolution and action plan; and a recommendation system configured to match one or more users and one or more items and provide an explanation of user behavior.

30. The system of claim 19, wherein the semiotics component is further configured to implement a neuro-symbolic architecture and to assign a named label to one or more of: a component of the system, a neuron of the explainable model, or a summary of the explanation.

* * * * *